US007258873B2

(12) United States Patent
Truong-Le et al.

(10) Patent No.: US 7,258,873 B2
(45) Date of Patent: Aug. 21, 2007

(54) PRESERVATION OF BIOACTIVE MATERIALS BY SPRAY DRYING

(75) Inventors: Vu Truong-Le, Campbell, CA (US); Binh Pham, Mountain View, CA (US)

(73) Assignee: MedImmune Vaccines, Inc., Mountain View, CA (US)

( * ) Notice: Subject to any disclaimer, the term of this patent is extended or adjusted under 35 U.S.C. 154(b) by 434 days.

(21) Appl. No.: 10/412,651

(22) Filed: Apr. 10, 2003

(65) Prior Publication Data

US 2003/0215515 A1 Nov. 20, 2003

Related U.S. Application Data

(60) Provisional application No. 60/447,683, filed on Feb. 14, 2003, provisional application No. 60/372,192, filed on Apr. 11, 2002.

(51) Int. Cl.
*A61K 9/14* (2006.01)

(52) U.S. Cl. ...................... 424/489; 424/490; 424/491; 424/493; 424/499

(58) Field of Classification Search .................... 435/2; 514/2; 424/93.7, 94.1, 400, 489, 490, 491, 424/493, 499
See application file for complete search history.

(56) References Cited

U.S. PATENT DOCUMENTS

| | | | |
|---|---|---|---|
| 4,972,995 | A | 11/1990 | Schara et al. |
| 5,272,820 | A | 12/1993 | Ito et al. |
| 5,301,664 | A | 4/1994 | Sievers et al. |
| 5,639,441 | A | 6/1997 | Sievers et al. |
| 5,902,844 | A | 5/1999 | Wilson |
| 6,051,256 | A | 4/2000 | Platz et al. |
| 6,063,910 | A | 5/2000 | Debenedetti et al. |
| 6,095,134 | A | 8/2000 | Sievers et al. |
| 6,136,346 | A | 10/2000 | Eljamal et al. |
| 6,165,463 | A | 12/2000 | Platz et al. |
| 6,258,341 | B1 | 7/2001 | Foster et al. |
| 6,268,053 | B1 | 7/2001 | Woiszwillo et al. |
| 6,284,282 | B1 | 9/2001 | Maa et al. |
| 6,299,906 | B1 | 10/2001 | Bausch et al. |
| 6,303,582 | B1 | 10/2001 | Eljamal et al. |
| 6,309,671 | B1 | 10/2001 | Foster et al. |
| 6,372,258 | B1 | 4/2002 | Platz et al. |
| 6,486,329 | B1 | 11/2002 | Albano et al. |
| 2002/0018815 | A1 | 2/2002 | Sievers et al. |

FOREIGN PATENT DOCUMENTS

| | | | |
|---|---|---|---|
| WO | WO9714407 | * | 4/1997 |

OTHER PUBLICATIONS

Yeo et al., Formation of Microparticulate Protein Powders Using a Supercritical Fluid Antisolvent, Biotechnology and Bioengineering, vol. 41: pp. 341-346 (1993).

* cited by examiner

*Primary Examiner*—Ruth A Davis
(74) *Attorney, Agent, or Firm*—Gary Baker; Quine Intellectual Property Law Group, P.C.

(57) ABSTRACT

This invention provides methods and compositions to preserve bioactive materials in a matrix of powder particles. Methods provide high-pressure gas spraying and/or near supercritical spraying of formulations followed by drying in a stream of conditioned gas to form stable powder particles containing bioactive materials.

39 Claims, 10 Drawing Sheets

PRESERVATION OF BIOACTIVE MATERIALS BY SPRAY DRYING

CROSS-REFERENCE TO RELATED APPLICATIONS

This application claims benefit of and priority to a prior U.S. Provisional Application No. 60/372,192, "Method of Spray-Drying Therapeutic Agents Using Supercritical Fluids", by Vu Truong-Le, filed Apr. 11, 2002; and to a prior U.S. Provisional Application No. 60/447,683, "Preservation of Bioactive Materials by Spray Drying", by Vu Truong-Le, filed Feb. 14, 2003. The full disclosure of the prior applications are incorporated herein by reference.

FIELD OF THE INVENTION

The present invention is in the field of preservation of biologic materials in storage. In particular, the invention relates to, e.g., preservation of bioactive molecules in matrices of spray dried powder particles.

BACKGROUND OF THE INVENTION

Biological materials, such as proteins, peptides, nucleic acids, bacteria, cells, antibodies, enzymes, serums, vaccines, liposomes, and viruses, are generally unstable when stored in media or other liquid solutions. For example, enveloped viruses such as live influenza virus manufactured from egg allantoid fluid loose one log of potency, defined as Tissue Culture Infectious Dose (TCID50), in less than two to three weeks when stored under refrigerated temperature, i.e. approximately 4° C. At room temperature conditions (approximately 25° C.) and at warmer temperatures such as 37° C., the virus looses the such potency in a matter of days to hours, respectively. Lyophilization processes, where aqueous formulas are frozen then dried by sublimation, are commonly used to stabilize these biological materials. Spray-drying is another process commonly used to remove water from biological materials for storage. Substitution of protectant molecules, such as carbohydrates, after removal of water can increase stability by preventing chemical degradation, denaturation, and growth of microbial contaminants.

In lyophilization (freeze-drying), the biological material is commonly mixed as a solution or suspension with protective agents, frozen, and dehydrated by sublimation and secondary drying. The low temperatures of freezing and drying by sublimation can slow the kinetics of degradation reactions but they can also reduce the ability of protective agents to penetrate certain biological materials. Moreover, the low temperatures and low surface to volume ratios involved in freeze drying can require long drying times.

Lyophilization and secondary drying processes can force a protein or cell, for example, to undergo significant chemical and physical changes. Such changes can result in loss of activity of the protein due to concentration of salts, precipitation/crystallization, shear stress, pH extremes, and residual moisture remaining through the freeze-drying. Freeze-drying can pierce cells with ice crystals and fail to protect internal compartments.

The formation of powder particles by grinding or lyophilized cakes or by spray drying is of substantial interest and importance to the biopharmaceutical industry for preservation of biologically active materials. Not only can such fine particles provide a convenient storage form for biomaterials such as proteins, non-protein biomolecules (including for example, DNA, RNA, lipids, and carbohydrates), but they can be substantially dehydrated for long-term storage and rewettable for administration of the biomaterial for its intended use after the storage period. Further, such dried fine particles could be produced in a controlled diameter range and may be administered as a dried aerosol power, for example, via the intranasal route, wherein the nasal mucosa would provide for rewetting and resolution of the biomaterial in a patient. Numerous other uses of such fine and microfine particles containing a biomaterial would find use in the art of pharmaceutics, biologics, and particularly in the field of live virus vaccines. Thus, it would be advantageous to develop methods of forming fine particles containing biologically active materials.

Spray drying is a well known process long used, e.g., in the food processing industry to produce powders. For example, liquid products, such as milk, are sprayed through a nozzle into a stream of hot gasses to produce a powder. The increased surface area exposed in the spray mist, in combination with the high temperatures of the drying gas, provides rapid removal of water from the liquid product. However, such process conditions are often unsuitable for sensitive biologic materials due to the shear stress, heat stress, oxidative stress, and conformational changes that can occur with loss of hydration water at high temperatures. Some of these problems are addressed in pharmaceutical spray drying methods, such as those described in U.S. Pat. No. 5,902,844, Spray Drying of Pharmaceutical Formulations Containing Amino Acid-Based Materials, to Wilson. In Wilson, peptides in solution with a water soluble polymer are sprayed into a stream of drying gas to form a pharmaceutical composition. The presence of the polymer can protect the peptide from degradation by coating the peptide against chemical attacks and by substituting for water of hydration lost during drying. Certain sensitive peptides and other biological materials, such as nucleic acids, bacteria, cells, antibodies, enzymes, serums, vaccines, liposomes, and viruses can still be damaged, however, by the heat, shear stress and dehydration of the processes described by Wilson, and the like.

Larger and more complex biologics, such as live virus and bacterial vaccines, are well recognized as being among the most unstable products. For example, enveloped viruses such as live influenza virus manufactured from egg allantoid fluid loose one log of potency, defined as Tissue Culture Infectious Dose (TCID50), in less than two to three weeks when stored under refrigerated temperature, i.e. approximately 4° C. At room temperature conditions (approximately 25° C.), the virus looses the such potency in a matter of days.

A need remains for methods to preserve sensitive biological materials, such as proteins and live viruses in storage, particularly at temperatures above freezing. Methods to prepare dry powder particles using processes with quick low temperature drying are desirable to suit the sensitivities of particular biologic materials. What's more, spray drying processes that do not require exposure to organic co-solvents can reduce denaturation of sensitive biological structures. Compositions that can protect such biologicals in storage would provide benefits in medicine and scientific research. The present invention provides these and other features that will become apparent upon review of the following.

SUMMARY OF THE INVENTION

The present invention includes methods, apparatus, and compositions for preserving bioactive materials in storage. The invention provides, e.g., spraying of a mixture with a high-pressure gas and/or near supercritical fluid, and spray drying under conditions that can provide fine dry powder particles with reduced shear or temperature stress on sensitive bioactive materials.

The methods of the invention generally include, e.g., spraying a bioactive material in suspension or solution mixed with a high pressure gas or near supercritical gas to provide fine particles under conditions of lower temperature and lower shear stress than typically experienced with ordinary spraying or atomization techniques. The fine droplets in the spray can be dried, e.g., faster, and at lower temperatures, than with ordinary techniques. Methods of the invention can provide, e.g., the ability to generate ultra fine droplet size, resulting in an increased droplet surface area to volume ratio for increased evaporation efficiency per given heat input. The method of preparing powder particles in the invention can comprise, for example, preparing an aqueous suspension or solution of a bioactive material and a polyol, forming a mixture of the solution or suspension with a pressurized gas or near supercritical fluid, spraying ultrafine droplets by depressurizing the mixture, and drying the droplets into powder particles by exchanging the spray gases with drying gases, e.g., to by spraying into a drying chamber of the spray dry apparatus.

The bioactive material in suspension or solution, for mixture and spraying in the method can be, e.g., a protein, a peptide, a nucleic acid, bacteria, cells, an antibody, an enzyme, serum, a vaccine, liposomes, a virus, and/or the like. Viruses for bioactive material suspensions of the method can include, e.g., influenza virus, parainfluenza virus, respiratory syncytial virus, herpes simplex virus, cytomegalo virus, SARS virus, corona virus family members, human metapneumovirus, and Epstein-Bar virus.

The polyol in suspensions or solutions for mixing and spraying in the method can be, e.g., trehalose, sucrose, sorbose, melezitose, glycerol, fructose, mannose, maltose, lactose, arabinose, xylose, ribose, rhamnose, palactose, glucose, mannitol, xylitol, erythritol, threitol, sorbitol, and raffinose. The suspension or solution can also include, e.g., a polymer, such as starch, starch derivatives, carboxymethyl starch, hydroxyethyl starch (HES), dextran, human serum albumin (HSA), and gelatin, to provide protection to the bioactive material and structure to the particle. A surfactant, such as, e.g., polyethylene glycol sorbitan monolaurate, polyoxyethylenesorbitan monooleate, or block copolymers of polyethylene and polypropylene glycol, can be added to the suspension or solution to increase the solubility of suspension or solution constituents, and/or to enhance reconstitution and stability of powder particles of the invention. Amino acid additives such as arginine, lysine, glycine, methionine, glutamine, histidine, and the like, can be useful stabilizers.

The suspensions or solutions of the invention can be mixed with a pressurized gas or a gas near supercritical conditions before spraying. High pressure gases called the invention can be, e.g., nitrogen, carbon dioxide, oxygen, propane, nitrous oxide, helium, hydrogen, and/or the like, at pressures ranging from about 100 pounds per square inch (psi) to about 15,000 psi, or about 1000 psi. Near supercritical can mean, e.g., a pressure ranging from about 90 percent and 110 percent of the critical pressure and/or temperature for the fluid. Where the near supercritical fluid is carbon dioxide, a typical pressure can be about 1200 psi. The near supercritical fluid in the method can be, e.g., carbon dioxide, sulfur hexafluoride, chlorofluorocarbons, fluorocarbons, nitrous oxide, xenon, propane, n-pentane, ethanol, nitrogen, water, and/or the like. The temperatures of the high-pressure gas or near supercritical fluid before mixture with the suspension or solution typically ranges from about 0° C. to about 60° C. A modifier, such as methanol, ethanol, isopropanol, or acetone can be added to the gas or the near supercritical fluid to, e.g., affect physical properties of the fluid and/or to influence primary drying of the suspension or solution.

Contact of high pressure or near supercritical gas with the solution or suspension in the mixture can provide, e.g., certain solvation and/or emulsification effects. For example, a solution of the gas, or liquid phase gas, can be formed in the suspension or solution when the gas is soluble to some significant degree in the suspension or solution. Optionally, the solution or suspension can be, e.g., dissolved to some extent in a liquid phase near supercritical gas. In another aspect, the suspension or solution can be, e.g., emulsified in the high pressure gas or near critical gas, or can be, e.g., or the high pressure gas or near critical gas can be emulsified in the suspension or solution. Control of such solvation or emulsification effects can be provided, e.g., by adjustment of mixture temperature, residence time in the mixing chamber, relative proportions of the solution or suspension and high pressure or near supercritical gas, flow rates, pressures, solution or suspension constituents, the presence of additional solvents, and/or the like.

Forming a mixture of the high-pressure gas and/or near supercritical fluid with the suspension or solution can take place, e.g., in a nozzle with a T-junction, a mixing chamber and/or a capillary restrictor. Forming a mixture can entail flowing the solution or suspension with the pressurized gas or near supercritical fluid through a mixing chamber. The mixing chamber can have passage configurations which, e.g., produce vortices or turbulence in the flowing mixture to increase the efficiency of mixing. Reducing the pressure (expansion) of the mixture to form a suspension of droplets in gas can result from, e.g., passage of the mixture through the nozzle and out from a spray orifice outlet of the capillary restrictor. The capillary restrictor can have, e.g., an internal diameter less that the mixing chamber; typically less than about 1000 um, ranging from about 50 um to about 500 um, or about 100 um.

A variety of parameters can be adjusted to modify the average size of the droplets. Droplet size can be influenced, e.g., by adjusting the near supercritical fluid pressure or pressure of the high-pressure gas, adjusting the suspension or solution pressure, adjusting the flow rate of the suspension or solution, choice of the nozzle conduit internal diameter, adjusting the temperature of the drying gas, adjusting the pressure inside the particle formation vessel, changing the concentrations of suspension or solution constituents, and/or the like. For example, the suspension or solution can be supplied to the mixing chamber at from about 0.5 ml/min to about 30 ml/min to spray from a 100 um internal diameter nozzle orifice; lower rates forming smaller droplets and faster rates forming larger droplets. In the methods, formation of droplets ranging in mass median diameter from about 1 um to about 200 um is preferred.

Following spray formation of droplets, primary and secondary drying convert the droplets into particles. Primary drying can begin, e.g., with decompression and expansion of the liquid-gas (solution or suspension—high pressure or near supercritical gas) mixture to form a gaseous suspension of droplets. The gas and evaporated solvents of the expanded mixture can then be exchanged with a drying gas, such as nitrogen at a temperature ranging from about 5° C. to about 90° C. Drying can include secondary drying, wherein, e.g., residual moisture is further reduced after gross primary water removal. Drying can be provided, e.g., in a cyclonic vortex or by suspension of powder particles in an updraft of drying gases to form a fluidized bed. To reduce static buildup and reduce possible particle agglomeration, counter ions can be injected into a chamber of dry or drying particles. Drying gases can be recycled, e.g., by reconditioning in heat exchangers and/or desiccators or condensers. At the end of drying, powder particles can have, e.g., an average size (MMD) ranging from about 0.5 um to about 200 um, or about 1 um to about 150 um, or about 5 um to about 20 um, with a moisture content of less than about 10 weight percent, and bioactive material stability in storage, e.g., for at least about nine months at about 25° C. or for at least about 2 years in storage at about 4° C. Live viruses, live bacteria, and live cells can retain at least about half, or at least about 10 percent of original viability in the powder particles after processing.

Particles can be transferred in streams of drying gas to chambers for drying, size separation, coating, collection, and/or the like. Powder particles can be collected by transferring them to a secondary drying chamber in a flowing stream of drying gas. The secondary drying chamber can be configured as a cyclonic vortex chamber to allow contact of particles with warm chamber surfaces and to extend contact time of the particles with the drying gas. The particles can be separated by size in the chamber, e.g., by differential settling. The particles can be coated, e.g., with a polymer to provide a protective coat. The particles can settle to a collection vessel at the bottom of the chamber to accumulate before recovery. Total process efficiency can be recovery of 50%, 70%, 80%, 90%, or more of the bioactive material mass and/or activity.

Recovered powder particles can be administered as a particle or as a reconstituted solution or suspension. The fine particles produced by the methods of the invention can be reconstituted into a suspension or solution with a bioactive material concentration greater than the original process suspension or solution. For example, the dried powder particles can be reconstituted at 2-30 times the concentration of the initial liquid feed (solution or suspension) without incurring significant activity loss or protein denaturation; the reconstitution times for 100 mg/ml solutions can be less than 5 minutes. The powder particles can be administered, e.g., to a mammal by intramuscular, intraperitoneal, intracerebrospinal, subcutaneous, intra-articular, intrasynovial, intrathecal, oral, topical, inhalation intranasal, and/or pulmonary administration routes.

The methods of the invention can be practiced, e.g., using the apparatus of the invention. The apparatus can have chambers to hold and mix the suspension or solutions and a pressurized gas or near supercritical fluid, before spraying the mixture from a nozzle into a particle formation vessel. Particles formed therein can be, e.g., dried in a stream of drying gas and/or transferred to secondary drying chambers configured to further dry, coat, sieve, size, and/or collect the particles. In one embodiment of the apparatus, for example, a first chamber contains the suspension or solution of bioactive material and a polyol, a second chamber contains the high pressure gas and/or near supercritical fluid, a mixing chamber is in fluid communication with the first chamber through a first conduit and with the second chamber through a second conduit, a capillary restrictor provides restricted fluid communication between the mixing chamber and a particle formation vessel, and a stream of a drying gas flows to dry the fine mist of droplets formed when the suspension or solution is mixed with the gas and/or near supercritical fluid in the mixing chamber and is sprayed into the particle formation vessel. The result can be a preparation of stable dry fine powder particles containing the bioactive material.

The suspension or solution of in the first chamber can include, e.g., a bioactive material, polyol, polymer, and a surfactant. The bioactive material can include, e.g., proteins, peptides, nucleic acids, bacteria, cells, antibodies, enzymes, serums, vaccines, liposomes, viruses, and/or the like. The polyol can be, e.g., trehalose, sucrose, sorbose, melezitose, glycerol, fructose, mannose, maltose, lactose, arabinose, xylose, ribose, rhamnose, palactose, glucose, mannitol, xylitol, erythritol, threitol, sorbitol, raffinose, and/or the like. The polymer can be, e.g., starch, starch derivatives, carboxymethyl starch, hydroxyethyl starch (HES), dextran, human serum albumin (HSA), gelatin, and/or the like. The surfactant can be, e.g., polyethylene glycol sorbitan monolaurate (Tween 20), polyoxyethylenesorbitan monooleate (Tween 80), block copolymers of polyethylene and polypropylene glycol (Pluronic), and/or the like. Amino acids additives such as arginine, lysine, glycine, methionine, glutamine, histidine, and the like can be useful stabilizers.

The gas and/or near supercritical fluid for mixture with the suspension or solution in the apparatus can be, e.g., nitrogen, carbon dioxide, oxygen, propane, carbon monoxide, fluorane, nitrous oxide, helium, hydrogen, sulfur hexafluoride, chlorofluorocarbons, fluorocarbons, nitrous oxide, xenon, propane, n-pentane, ethanol, nitrogen, and/or water.

The suspension or solution, and the high-pressure gas and/or near supercritical fluid, can be fed to a nozzle of the apparatus to form a mixture that is sprayed into the particle formation vessel of the apparatus. A first flow control means, such as a pump or valve, can be connected to the first conduit between the first chamber and the mixing chamber to control flow of suspension or solution into the mixing chamber. A second flow control means, such as a pump or valve, can be connected to the second conduit between the second chamber and the mixing chamber to control flow of the gas and/or near supercritical fluid into the mixing chamber. The inlets into the mixing chamber from the first conduit and/or second conduit can be directed at an angle less than 90 degrees from an axis of the mixing chamber. A capillary restrictor can provide, e.g., back pressure to the flowing mixture and an orifice to spray the mixture from the nozzle. The capillary restrictor can have, e.g., an internal diameter less than the mixing chamber; typically, the capillary restrictor can have an internal diameter ranging from about 50 um to about 1000 um, from about 50 um to about 500 um, or about 100 um. The nozzle can include, e.g., multiple capillary constrictors. The nozzle can have intersections for multiple feed channels to accommodate mixture of more than one gas and/or more than one liquid feed.

The mist of fine droplets formed as the mixture is sprayed from the nozzle can be dried by a drying gas. The particle formation vessel can act as a secondary drying chamber, or can be in fluid contact with a secondary drying chamber where particles can be transferred and dried by contact the drying gas and/or chamber surfaces. The dying gas can be, e.g., nitrogen gas controlled for temperature and/or humidity. The drying gas (inlet gas) can be, e.g., at a temperature less than a glass transition temperature of the powder particles.

Residual moisture in the particles can be reduced to stabilizing levels in a secondary drying chamber. The secondary drying chamber can be configured to act as a cyclonic vortex, a fluidized bed of powder particles, a chamber to spray protective coating material onto powder particles, a size separation device, and/or a particle collection vessel. Drying gasses can be recycled through the particle formation vessel and/or secondary drying chamber after removing moisture in a condenser or desiccator. Separation of particles by size in the apparatus can be by, e.g., differential settling, surface impact, or filtration, to produce powder particles range in average size (MMD) from about 1 um to about 150 um, or about 10 um. An ion generator can be included in the apparatus to neutralize static charges.

The present invention includes compositions, such as suspensions or solutions of a bioactive material, a polyol, a polymer additive, an amino acid additive, and/or a surfactant, for mixture with a high-pressure gas and/or a near supercritical fluid to form spray dried powder particles with improved stability. The suspensions or solutions can include other ingredients, such as buffers, carriers, excipients, and/or stabilizers. In one embodiment, the composition is a suspension of influenza virus in an aqueous solution of sucrose, HES, and a block copolymer of polyethylene and polypropylene glycol (Pluronic).

The suspension or solution formulation can include bioactive material, such as proteins, peptides, nucleic acids, bacteria, cells, antibodies, enzymes, serums, vaccines, liposomes, and viruses. The bioactive material can be present in an amount ranging, e.g., from less than about 0.00001 weight percent to about 30 weight percent or more of the suspension or solution. In the case of viral bioactive materials, the viruses can be, e.g., influenza virus, parainfluenza virus, respiratory syncytial virus, herpes simplex virus, SARS (severe acute respiratory syndrome) virus, corona virus family members, cytomegalo virus, human metapneumovirus, and Epstein-Bar virus. Live viruses can be present in the suspension or solution in a titer ranging, e.g., from about $10^3$ $TCID_{50}$ to about $10^{12}$ $TCID_{50}$/ml, or about $10^6$ $TCID_{50}$/ml. Viruses can be present in the dried particles in an amount, e.g., of about $10^2$ $TCID_{50}$/g, about $10^2$ $TCID_{50}$/g, about $10^3$ $TCID_{50}$/g, about $10^4$ $TCID_{50}$/g, about $10^5$ $TCID_{50}$/g, about $10^6$ $TCID_{50}$/g, about $10^7$ $TCID_{50}$/g, about $10^8$ $TCID_{50}$/g, about $10^9$ $TCID_{50}$/g, about $10^{10}$ $TCID_{50}$/g, or about $10^{11}$ $TCID_{50}$/g.

The suspension or solution of the invention can include any of a variety of non-reducing or reducing polyols, such as, e.g., trehalose, sucrose, sorbose, melezitose, glycerol, fructose, mannose, maltose, lactose, arabinose, xylose, ribose, rhamnose, palactose, glucose, mannitol, xylitol, erythritol, threitol, sorbitol, and raffinose. The polyol can be present in the suspension or solution, e.g., in an amount ranging from about 1 weight percent to about 40 weight percent. In a particular embodiment, the polyol is sucrose present in an amount of about 10 weight percent of the suspension or solution.

Polymers can be present in the suspensions or solutions of the invention. Exemplary polymers are hydrophilic biopolymers, such as starch, starch derivatives, carboxymethyl starch, hydroxyethyl starch (HES), dextran, human serum albumin (HSA), gelatin, and/or the like. Polymers with a molecular weight ranging from about 1 kDa to about 300 kDa are often preferred. Polymers are typically present in suspensions of the invention in concentrations ranging from about 0.5 weight percent to about 10 weight percent. In one embodiment, the suspension or solution contains HES at a concentration of about 5 weight percent.

Surfactants can be present in the suspensions or solutions of the invention, e.g., to enhance the solubility of formulation constituents, to aid in spraying fine particles, to stabilize bioactive materials, and/or to improve the reconstitution time of the dried particles. The suspensions or solutions of the invention can include nonionic surfactants, such as alkylphenyl alkoxylates, alcohol alkoxylates, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, fatty acid amides, methylcellulose, fatty acid esters, silicone oils, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers, polyethylene glycol sorbitan monolaurate, and/or polyoxyethylene-sorbitan monooleate. The suspensions or solutions of the invention can include ionic surfactants, such as alkylarylsulfonates, phenylsulfonates, alkyl sulfates, alkyl sulfonates, alkyl ether sulfates, alkyl aryl ether sulfates, alkyl polyglycol ether phosphates, polyaryl phenyl ether phosphates, alkylsulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde, condensates of sulfonated naphthalenes with formaldehyde and phenol, lignin-sulfite waste liquor, alkyl phosphates, quaternary ammonium compounds, amine oxides, and betaines. Surfactants can be present in the suspensions or solutions in amounts ranging, e.g., from about 0.001 weight percent to about 5 weight percent, or from about 0.01 weight percent to about 1 weight percent.

The suspension or solution (liquid feed material) of the invention can further comprise an amino acid stabilizer additive such as lysine, arginine, glycine, methionine, histidine, ant the like. The suspension or solution can include a buffer, such as a phosphate salt, a carbonate salt, a borate salt, an acetate salt, histidine, glycine, a citrate salt, and/or the like, to provide a pH, e.g., from about pH 3 to about pH 8. The buffers can be present at a concentration ranging from about 2 mM to about 500 mM, as appropriate.

The present invention includes, e.g., articles of manufacture comprising a container containing dried powder particles prepared by spray drying a mixture of high-pressure gas and/or near supercritical gas with a suspension or solution of bioactive material, a polyol, a polymer additive, and a surfactant.

DEFINITIONS

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a surface" includes a combination of two or more surfaces; reference to "bacteria" includes mixtures of bacteria, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

"Ambient" temperatures or conditions are those at any given time in a given environment. Typically, ambient room temperature is approximately 22° C., ambient atmospheric pressure, and ambient humidity are readily measured and will vary depending on the time of year, weather conditions, altitude, etc.

"Boiling" refers, e.g., to the rapid phase transition from liquid to gas that takes place when the temperature of a liquid is above its boiling temperature. The boiling temperature, as is well known to those skilled in the art, is the temperature at which the vapor pressure of a liquid is equal to the applied pressure.

"Buffer" refers to a buffered solution that resists changes in pH by the action of its acid-base conjugate components. The pH of the buffer will generally be chosen to stabilize the active material of choice, and will be ascertainable by those in the art. Generally, this will be in the range of physiological pH, although some proteins, can be stable at a wider range of pHs, for example acidic pH. Thus, preferred pH ranges are from about 1 to about 10, with from about 3 to about 8 being particularly preferred; more preferably, from about 6.0 to about 8.0; yet more preferably, from about 7.0 to about 7.4; and most preferably, at about 7.0 to about 7.2. Suitable buffers include a pH 7.2 phosphate buffer and a pH 7.0 citrate buffer. As will be appreciated by those in the art, there are a large number of suitable buffers that may be used. Suitable buffers include, but are not limited to, amino acids, potassium phosphate, sodium phosphate, sodium acetate, histidine-HCl, sodium citrate, sodium succinate, ammonium bicarbonate and carbonate. Generally, buffers are used at molarities from about 1 mM to about 2 M, with from about 2 mM to about 1 M being preferred, and from about 10 mM to about 0.5 M being especially preferred, and 25 to 50 mM being particularly preferred.

"Degassing" refers to the release of a gas from solution in a liquid when the partial pressure of the gas is greater than the applied pressure. If water is exposed to nitrogen gas at one atmosphere (about 760 Torr), and the partial pressure of nitrogen in the water equilibrates to the gas phase pressure, nitrogen can bubble from the water if the gas pressure is reduced. This is not boiling, and can often occur at pressures above a pressure that would boil a solvent. For example, bottled carbonated soft drinks, with a high partial pressure of $CO_2$ gas, bubble rapidly when pressure is reduced by removing the bottle cap.

"Dispersibility" means the degree to which a powder composition can be dispersed (i.e. suspended) in a current of air so that the dispersed particles can be respired or inhaled into the lungs of a subject. Thus, a powder that is 20% dispersible means that only 20% of the mass of the powder is suspendable by an inhalation device for inhalation into the lungs.

"Dry" in the context of dried powder compositions refers to residual moisture content less than about 10%. Dried powder compositions are commonly dried to residual moistures of 5% or less, or between about 3% and 0.1%. "Dry" in the context of particles for inhalation means that the composition has a moisture content such that the particles are readily dispersible in an inhalation device to form an aerosol.

"Excipients" generally refer to compounds or materials that are added to increase the stability of the therapeutic agent during the spray freeze dry process and afterwards, for long term physical stability and flowability of the powder product. Suitable excipients can be, e.g., agents that do not thicken or polymerize upon contact with water, are basically innocuous when inhaled by a patient and do not significantly interact with the therapeutic agent in a manner that alters its biological activity. Suitable excipients are described below and include, but are not limited to, proteins such as human and bovine serum albumin, gelatin, immunoglobulins, carbohydrates including monosaccharides (galactose, D-mannose, sorbose, etc.), disaccharides (lactose, trehalose, sucrose, etc.), cyclodextrins, and polysaccharides (raffinose, maltodextrins, dextrans, etc.); an amino acid such as monosodium glutamate, glycine, alanine, arginine or histidine, as well as hydrophobic amino acids (tryptophan, tyrosine, leucine, phenylalanine, etc.); a methylamine such as betaine; an excipient salt such as magnesium sulfate; a polyol such as trihydric or higher sugar alcohols, e.g. glycerin, erythritol, glycerol, arabitol, xylitol, sorbitol, and mannitol; propylene glycol; polyethylene glycol; Pluronics; surfactants; and combinations thereof. Excipients can be multifunctional constituents of solutions or suspensions of invention.

"Glass" or "glassy state" or "glassy matrix," refers to a liquid that has a markedly reduced ability to flow, i.e. it is a liquid with a very high viscosity, wherein the viscosity ranges from $10^{10}$ to $10^{14}$ pascal-seconds. It can be viewed as a metastable amorphous system in which the molecules have vibrational motion but have very slow (almost immeasurable) rotational and translational components. As a metastable system, it is stable for long periods of time when stored well below the glass transition temperature. Because glasses are not in a state of thermodynamic equilibrium, glasses stored at temperatures at or near the glass transition temperature relax to equilibrium and lose their high viscosity. The resultant rubbery or syrupy, flowing liquid is often chemically and structurally destabilized. While a glass can be obtained by many different routes, it appears to be physically and structurally the same material by whatever route it was taken. The process used to obtain a glassy matrix for the purposes of this invention is generally a solvent sublimation and/or evaporation technique.

The "glass transition temperature" is represented by the symbol $T_g$ and is the temperature at which a composition changes from a glassy or vitreous state to a syrup or rubbery state. Generally $T_g$ is determined using differential scanning calorimetry (DSC) and is standardly taken as the temperature at which onset of the change of heat capacity (Cp) of the composition occurs upon scanning through the transition. The definition of $T_g$ is always arbitrary and there is no present international convention. The $T_g$ can be defined as the onset, midpoint or endpoint of the transition; for purposes of this invention we will use the onset of the changes in Cp when using DSC and DER. See the article entitled "Formation of Glasses from Liquids and Biopolymers" by C. A. Angell: Science, 267, 1924-1935 (Mar. 31, 1995) and the article entitled "Differential Scanning Calorimetry Analysis of Glass Transitions" by Jan P. Wolanczyk: Cryo-Letters, 10, 73-76 (1989). For detailed mathematical treatment see "Nature of the Glass Transition and the Glassy State" by Gibbs and DiMarzio: Journal of Chemical Physics, 28, NO. 3, 373-383 (March, 1958). These articles are incorporated herein by reference.

"Penetration enhancers" are surface active compounds that promote penetration of a drug through a mucosal membrane or lining and are generally used intranasally, intrarectally, and intravaginally.

"Pharmaceutically acceptable" excipients (vehicles, additives) are those which can reasonably be administered to a subject mammal to provide an effective dose of the active ingredient employed. Preferably, these are excipients which the Federal Drug Administration (FDA) have to date designated as 'Generally Regarded as Safe' (GRAS).

"Pharmaceutical composition" refers to preparations which are in such a form as to permit the biological activity of the active ingredients to be unequivocally effective, and which contain no additional components which are toxic to the subjects to which the composition would be administered.

"polyol" is a substance with multiple hydroxyl groups, and includes sugars (reducing and nonreducing sugars), sugar alcohols and sugar acids. Preferred polyols herein have a molecular weight which is less than about 600 kDa (e.g. in the range from about 120 to about 400 kDa). A "reducing sugar" is a polyol which contains a hemiacetal group that can reduce metal ions or react covalently with lysine and other amino groups in proteins. A "nonreducing sugar" is a sugar which does not have these properties of a reducing sugar. Examples of reducing sugars are fructose, mannose, maltose, lactose, arabinose, xylose, ribose, rhamnose, galactose and glucose. Nonreducing sugars include sucrose, trehalose, sorbose, melezitose and raffinose. Mannitol, xylitol, erythritol, threitol, sorbitol and glycerol are examples of sugar alcohols. As to sugar acids, these include L-gluconate and metallic salts thereof.

"Powder" means a composition that consists of finely dispersed solid particles that are relatively free flowing and capable of being readily dispersed in an inhalation device and subsequently inhaled by a patient so that the particles are suitable for intranasal or pulmonary administration via the upper respiratory tract including the nasal mucosa.

"Recommended storage temperature" for a composition is the temperature at which a powdered drug composition is to be stored to maintain the stability of the drug product over the shelf life of the composition in order to ensure a consistently delivered dose. This temperature is initially determined by the manufacturer of the composition and approved by the governmental agency responsible for approval the composition for marketing (e.g., the Food and Drug Administration in the U.S.). This temperature will vary for each approved drug product depending on the temperature sensitivity of the active drug and other materials in the product. The recommended storage temperature will vary from less than about 0° to about 40° C., but generally will be ambient temperature, i.e. about 25° C. Usually a drug product will be kept at a temperature that is at or below the recommended storage temperature.

A biologically active material "retains its biological activity" in a pharmaceutical composition, if the biological activity of the biologically active material, such as an enzyme, at a given time is within about 10% (within the errors of the assay) of the biological activity exhibited at the time the pharmaceutical composition was prepared as determined in a binding assay, for example. For proteins, such as antibodies, purity by analytical techniques such as size exclusion HPLC, FTIR, DSC, CD, ELISA, can be correlated to biological activity. In the case of living viruses, biological activity can be considered retained when the viral titer of the composition is within one log of the initial titer. The assay that is used to determine live influenza virus titer is the Fluorescent Focus Assay (FFA assay). The titer from this assay is reported as Fluorescent Focus Unit per milliliter (FFU/ml). One FFU/ml is approximately equal to one Tissue Culture Infectious Dose per ml ($TCID_{50}$/ml). Other "biological activity" assays are elaborated below.

A biologically active material "retains its chemical stability" in a pharmaceutical composition, e.g., if the chemical stability at a given time is such that the biologically active material is considered to still retain its biological activity as defined above. Alternately, chemical stability can be defined, e.g., as no significant change in the structure of a biological material as accessed by appropriate analytical techniques. Chemical stability can be assessed by detecting and quantifying chemically altered forms of the biologically active material. Chemical alteration may involve size modification (e.g. clipping of proteins) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography, for example.

A biologically active material "retains its physical stability" in a pharmaceutical composition if, e.g., it shows no significant increase in aggregation, precipitation and/or denaturation upon visual examination of color and/or clarity, or as measured by UV light scattering or by size exclusion chromatography.

"stable" formulation or composition is one in which the biologically active material therein essentially retains its physical stability and/or chemical stability and/or biological activity upon storage. Various analytical techniques for measuring stability are available in the art and are reviewed, e.g., in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period. Trend analysis can be used to estimate an expected shelf life before a material has actually been in storage for that time period. For live influenza viruses, stability is defined as the time it takes to loose 1 log of FFU/ml or 1 log of TCID50/ml. Preferably, the composition is stable at room temperature (~25° C.) for at least 3 months, and/or stable at about 2-8° C. for at least 1 year. Furthermore, the composition is preferably stable following freezing (to, e.g., −70° C.) and thawing of the composition.

High pressure gas or near supercritical drying, as used herein, refers to removal of a solvent, such as water or organic reagents, from a suspension or solution mixed with a high-pressure gas or a near supercritical fluid. The high pressure or supercritical drying can include, e.g., mixing of the solution or solvent containing the active ingredient with the pressurized gas or the supercritical fluid to form a mixture of liquid and gas, spraying of the suspension or solution by depressurization, expansion, or degassing of the gas-liquid mixture to generate fine droplets. Many supercritical fluids such as, for example, supercritical carbon dioxide, may be used in the supercritical drying process.

"Near supercritical fluid" refers to a fluid held at, or within about 10%, of a critical point pressure and/or temperature (in degree Kelvin). A critical point is a combination of temperature and pressure wherein a substance can no longer exist as a liquid if the temperature (critical temperature) is increased or the pressure (critical pressure) is lowered. The critical temperature is the temperature above which a gas cannot be liquefied; the temperature above which a substance cannot exhibit distinct gas and liquid phases for a given pressure. The critical pressure is the pressure required to liquefy a gas (vapor) at a critical temperature. For example, the critical pressure and temperature of carbon dioxide are 74 atmospheres and 31 degrees Centigrade, respectively. Carbon dioxide held at a pressure and temperature above its critical point is in a supercritical condition or state. Critical pressures and temperatures for other substances are provided below:

| Fluid | Pc (bar) | Tc (° C.) |
|---|---|---|
| Carbon dioxide | 74 | 31 |
| Nitrous oxide | 72 | 36 |
| Sulfur hexafluoride | 37 | 45 |
| Xenon | 58 | 16 |
| Ethylene | 51 | 10 |
| Chlorotrifluoromethane | 39 | 29 |
| Ethane | 48 | 32 |
| Trifluoromethane | 47 | 26 |

In a pharmacological sense, a "therapeutically effective amount" of a biologically active material refers to an amount effective in the prevention or treatment of a disorder wherein a "disorder" is any condition that would benefit from treatment with the biologically active material. This includes chronic and acute disorders or diseases including those pathological conditions which predispose the mammal to the disorder in question.

"Treatment" refers to both therapeutic treatment and prophylactic or preventative measures. Those in need of treatment include those already with the disorder as well as those in which the disorder is to be prevented.

"Unit dosage" refers to a receptacle containing a therapeutically effective amount of a composition of the invention.

BRIEF DESCRIPTION OF THE DRAWINGS

FIG. 8 shows the long term stability of live B/Harbin influenza virus spray dried in formulation AVO47a.

DETAILED DESCRIPTION

Figure 1A:
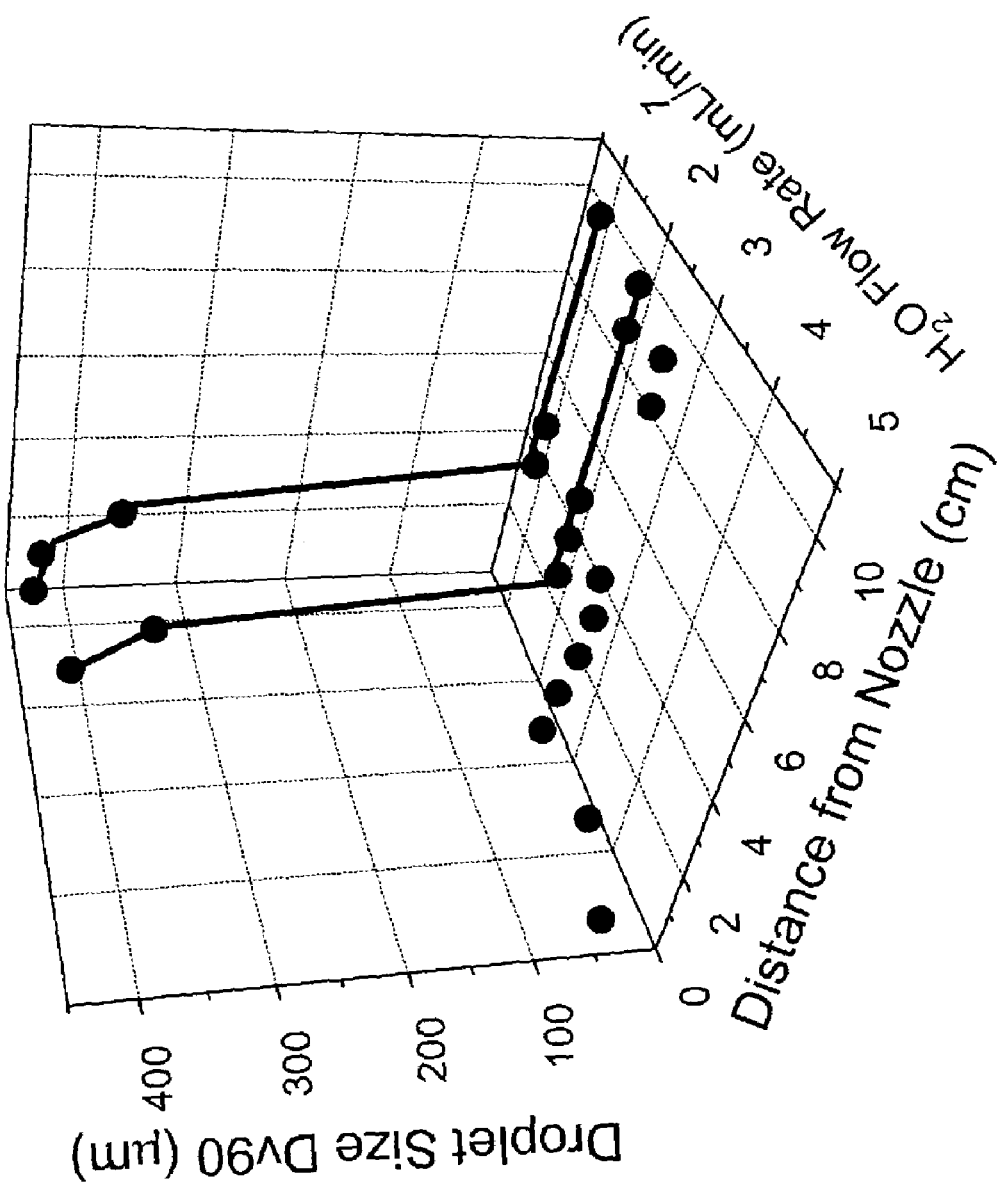
FIGS. 1A and 1B show droplet sizes from a 100 micron fused silica nozzle when sprayed using near supercritical CO2 as a function of distance from the nozzle tip.

The methods, apparatus, and compositions of the present invention can provide high initial purity and extended storage of bioactive materials in a matrix of dry powder particles. The method provides, e.g., quick drying of droplets into particles without high heat by, e.g., mixing a formulation of a bioactive material with a high-pressure gas and/or near supercritical gas in a mixing chamber before spraying from a nozzle to produce a fine mist. Solvents can evaporate rapidly from the mist droplets leaving dry particles that can further dehydrated in a secondary drying chamber. The formulations of the invention include, e.g., suspensions or solutions of the bioactive material with polyols, polymers, amino acids, and/or surfactants, that can dry into a stable preservative matrix.

Methods of Preparing Powder Particles

Methods of the invention include, e.g., mixture of a bioactive material suspension or solution with a near supercritical fluid and/or high pressure gas, expansion of the mixture to form a fine mist (gaseous suspension) of droplets, and drying of the droplets to powder particles in a particle formation vessel and/or secondary drying chamber. Expansion of the suspension or solution from the mixture with the near supercritical gas can produce very fine droplets under conditions of low shear stress, and relatively low temperature. The rapid removal of water during the expansion, and the fine particle size, allow relatively mild drying conditions in the particle formation vessel and/or secondary drying chamber. Low shear spraying, low temperature primary drying, and/or moderate secondary drying conditions can reduce process degradation of bioactive materials in the powder particles and increase stability of the particles in storage.

Methods of preparing powder particles in the invention include, e.g., preparation of a solution or suspension, mixture with a high pressure gas and/or a near supercritical fluid, spraying into a particle formation chamber for primary drying, secondary drying of the particles, and recovery of dried stable powder particles. The aqueous suspension or solution can contain, e.g., a bioactive material, a polyol, a polymer, an amino acid, and a surfactant. The near supercritical fluid can be, e.g., carbon dioxide. The mixture can be formed, e.g., in a mixing chamber adjacent to a capillary restrictor spray nozzle outlet. The expansion of gas during spraying can disrupt the suspension or solution into fine droplets that dry rapidly. Secondary drying can be by, e.g., suspension of particles in a vortex or fluidized bed of temperature/humidity controlled gas. The powder particle product can be recovered, e.g., by settling after sizing.

Preparing a Suspension or Solution

Suspensions or solutions (liquid feed materials) of the invention can include, e.g., a bioactive material formulated with a polyol, polymer, surfactant, amino acid, and/or buffer, in an aqueous solution. The ingredients can be combined in a sequence using techniques appropriate to the constituents, as is appreciated by those skilled in the art. For example, a bioactive material, such as a virus or bacterium, can be, e.g., concentrated and separated from growth media by centrifugation or filtration before mixture with a polyol solution to form a suspension. Antibodies can be purified and concentrated, e.g., by affinity chromatography before dissolving into a solution with other formulation ingredients. Liquid suspensions or solutions for spraying can be prepared by mixing the bioactive material, polyols, and other excipients, in an aqueous solution. Some bioactive materials, such as, e.g., peptides and antibodies, dissolve readily into an aqueous solution. Other bioactive materials, such as, e.g., bacteria and liposomes can be particles that exist as a suspension. Whether the bioactive material provides a solution or suspension, it is often he suspension or solution can also include, e.g., a polymer, such as starch, starch derivatives, carboxymethyl starch, hydroxyethyl starch (HES), dextran, human serum albumin (HSA), and gelatin, to provide protection to the bioactive material and structurly, then gently blended with the bioactive material after cooling.

The bioactive materials of the invention can be, e.g., industrial reagents, analytical reagents, vaccines, pharmaceuticals, therapeutics, and the like. Bioactive materials of the invention include, e.g., proteins, peptides, nucleic acids, bacteria, cells, antibodies, enzymes, serums, vaccines, liposomes, viruses, and/or the like. The bioactive material can be, e.g., living cells and/or viable viruses. The bioactive material can be, e.g., nonliving cells or liposomes useful as vaccines or as delivery vehicles for therapeutic agents. Viral bioactive materials of the invention can be, e.g., live viruses such as, influenza virus, parainfluenza virus, respiratory syncytial virus, herpes simplex virus, SARS virus, corona virus family members, cytomegalovirus, human metapneumovirus, Epstein-Barr virus, and/or the like. Preparation steps for solution or suspension liquid formulations of these materials can vary depending on the unique sensitivities of each material.

The concentration of bioactive materials in the suspension or solution can vary widely, depending, e.g., on the specific activity, concentration of excipients, route of administration, and/or intended use of the material. Where the bioactive material is a peptide vaccine, live virus or bacteria, for example, the required concentration of material can be quite low. Where the bioactive material is, e.g., an antibody for therapeutic administration by inhalation, or a liposome for topical administration, the required concentration can be higher. In general, bioactive materials can be present in the solutions or suspensions of the invention at a concentration, e.g., between less than about 1 pg/ml to about 150 mg/ml, from about 5 mg/ml to about 80 mg/ml, or about 50 mg/ml, as appropriate.

The suspensions or solutions of bioactive materials can include, e.g., any of a variety of polyols. In the methods of the invention, polyols can provide, e.g., a viscosity enhancing agent to reduce the effects of shear stress during spraying. The polyols can provide protective barriers and chemistries to the dry powder particles of the invention. For example, the polyol, such as sucrose, can physically surround and protect the bioactive material from exposure to damaging light, oxygen, moisture, and/or the like. The polyols can, e.g., replace water of hydration lost during drying, to prevent denaturation of biomolecules of the material. Although the invention is not limited to any particular polyols, the suspensions or solutions, and powder particle compositions, can include, e.g., sucrose, trehalose, sorbose, melezitose, sorbitol, stachyose, raffinose, fructose, mannose, maltose, lactose, arabinose, xylose, ribose, rhamnose, galactose, glucose, mannitol, xylitol, erythritol, threitol, sorbitol, glycerol, L-gluconate, and/or the like. Where it is desired that the formulation be freeze-thaw stable, the polyol is preferably one which does not crystallize at freezing temperatures (e.g. −20° C.) such that it destabilizes the biologically active material in the formulation. The amount of polyol used in the formulation will vary depending on the nature of the biologically active agent, other excipients, and intended use. However, the suspensions or solutions generally include a nonreducing sugar in a concentration between about 1% and 40%; more preferably, between about 1 and 20%. In a particularly preferred embodiment, the suspension or solution comprises about 10% sucrose.

Polymers can be included in the suspensions or solutions of the method, e.g., to provide protective and structural benefits. As with polyols, polymers can provide, e.g., physical and chemical protection to the bioactive materials. The linear or branching strands of polymers can provide, e.g., increased structural strength to the particle compositions of the invention. Polymers can be applied as a protective and/or time release coat to the outside or powder particles of the invention. Many polymers are, e.g., highly soluble in water, so they do not significantly hinder reconstitution of powder particles. Many polymers such as polyvinyl pyrrolidone, polyethylene glycol, poly amino acids, such poly L-lysines, can significantly enhance reconstitution rates in aqueous solutions. Polymer protective agents, in the methods of the invention can include, e.g., starch and starch derivatives, such as oxidized starch, carboxymethyl starch and hydroxyethyl starch. (HES), hydrolyzed gelatin, unhydrolyzed gelatin, ovalbumin, collagen, chondroitin sulfate, a sialated polysaccharide, actin, myosin, microtubules, dynein, kinetin, human serum albumin, and/or the like. Preferably, HES is used with a molecular weight of between about 100,000 and 300,000; and more preferably, about 200,000. Generally, the concentration of HES will be from about 0.5 to about 10%; more preferably, between about 1 and 5%. A preferred formulation comprises about 5% HES.

The suspension or solution of the invention can include, e.g., a surfactant compatible with the particular bioactive material involved. A surfactant can enhance solubility of other formulation components to avoid aggregation or precipitation at higher concentrations. Surface active agents can, e.g., lower the surface tension of the suspension or solution so that bioactive materials are not denatured at gas-liquid interfaces, and/or so that finer droplets can be formed during spraying. The suspensions or solutions according to the invention comprise between about 0.001 and 5%; and preferably, between about 0.05 and 1%, or about 0.2%, of a nonionic surfactant, an ionic surfactant, or a combination thereof.

Buffers can be added to the formulations of the method, e.g., to provide a suitable stable pH to the formulations of the method and compositions of the invention. Typical buffers of the invention include, e.g., amino acids, potassium phosphate, sodium phosphate, sodium acetate, sodium citrate, histidine, glycine, sodium succinate, ammonium bicarbonate, and/or a carbonate. The buffers can be adjusted to the appropriate acid and salt forms to provide, e.g., pH stability in the range from about pH 3 to about pH 10, from about pH 4 to about pH 8. A pH near neutral, such as, e.g., pH 7.2, is preferred for many compositions.

Other excipients can be included in the formulation. For example, amino acids, such as arginine and methionine can be constituents of the formulation and compositions. The amino acids can, e.g., act as zwitterions that block charged groups on processing surfaces and storage containers preventing nonspecific binding of bioactive materials. The amino acids can increase the stability of compositions by, e.g., scavenging oxidation agents, scavenging deamidation agents, and stabilizing the conformations of proteins. In another example, glycerol can be included in the formulations of the invention, e.g., to act as a polyol and/or plasticizer in the powder particle compositions. EDTA can be included in the composition, e.g., to reduce aggregation of formulation constituents and/or to scavenge metal ions that can initiate destructive free radical chemistries.

Mixing and Spraying

The suspension or solution of the invention is, e.g., mixed in a chamber with a high-pressure gas or a near supercritical fluid before spraying through a capillary restrictor nozzle outlet to form a fine mist of droplets. Without being bound to a particular theory, the combination of a high pressure gas or a near supercritical fluid with the suspension or solution can provide an emulsion mixture of droplets saturated and/or surrounded with fluid under pressure. As the mixture is released from the spray nozzle, the pressure drops rapidly allowing an explosive expansion, and/or effervescence (degassing), that disrupts the droplets into a fine mist (gaseous suspension of droplets). Such a mist can be, e.g., finer than would result with spraying at a lower pressure (e.g. less than 100 psi) or spraying without a near supercritical fluid. The droplets can experience, e.g., cool temperatures during any phase transition or adiabatic expansion associated with the decompression of the mixture. Shear stress can less than with hydraulic spraying (i.e., spraying liquid without gas) at a pressure high enough to provide the same fine droplets.

The suspensions or solutions are combined with a near supercritical fluid and/or high-pressure gas, e.g., in a mixing chamber before spraying to expand in a particle formation chamber. The suspension or solution can be held in a container (first chamber) and supplied through a conduit to the mixing chamber. The suspension or solution can be forced into the mixing chamber, e.g., by pressurization of the container or by pumping through high pressure pump. The high-pressure gas and/or near supercritical fluid can be supplied to the mixing chamber, e.g., through a conduit from a pressurized vessel (second chamber). The mixing chamber can be, e.g., an expanded conduit within the nozzle structure configured to produce vortices or turbulence in the flowing mixture. Depending, for example, on the gas or fluid, and the suspension or solution constituents, the bioactive material can exist as a particle, emulsion, precipitate, and/or solute in the mixture.

Figure 1B:
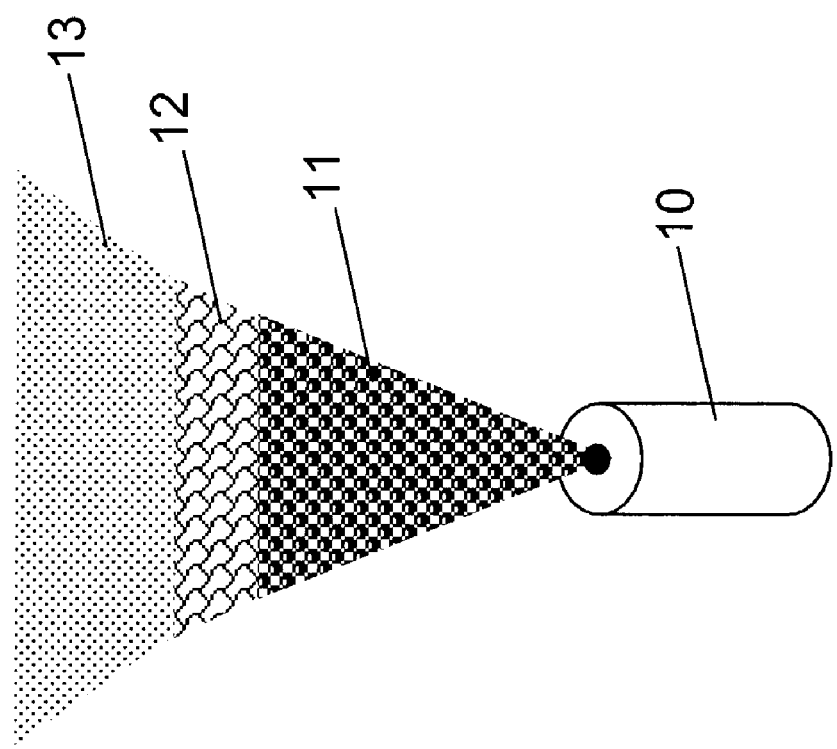
Figure 2:
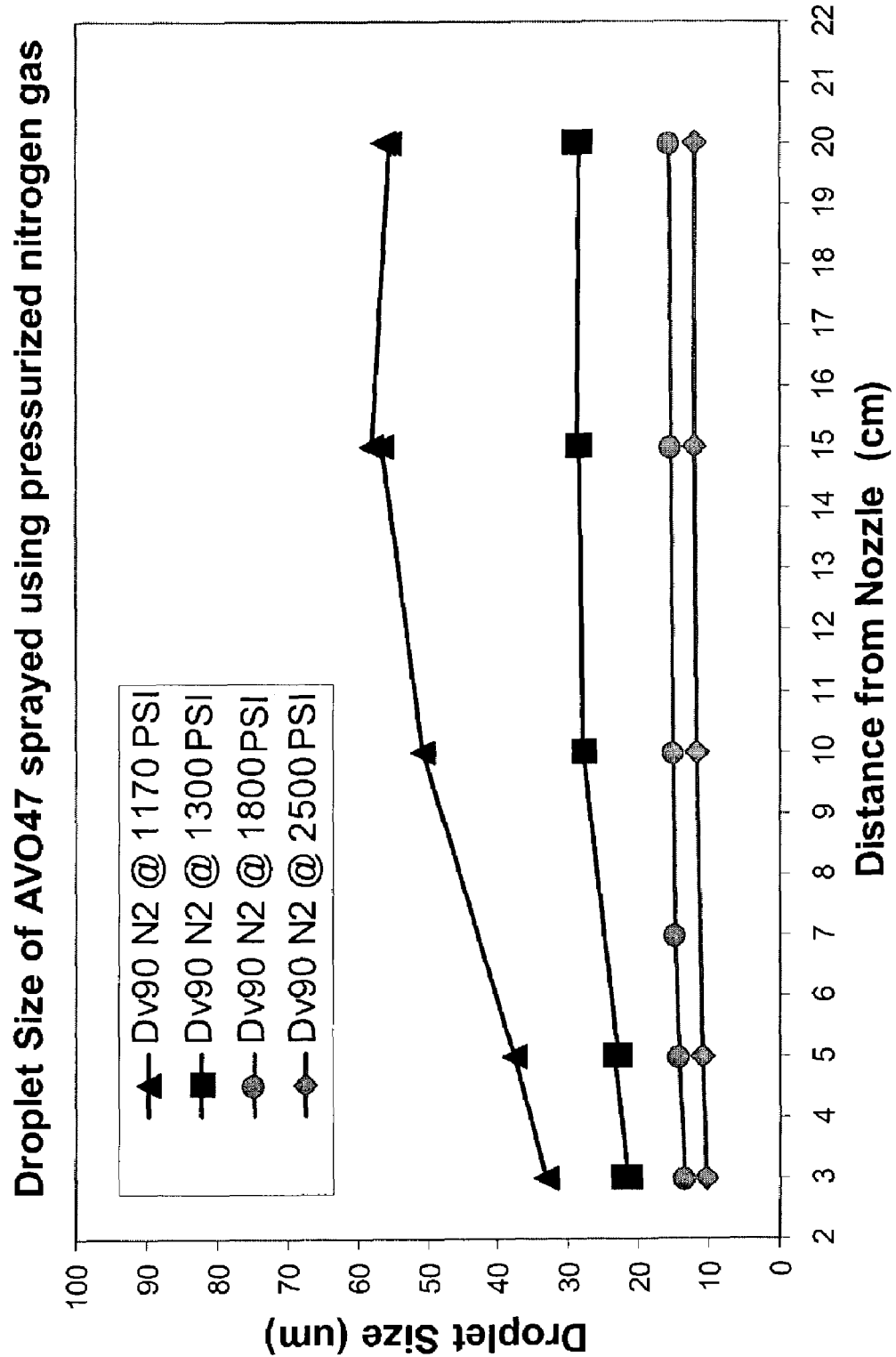
FIG. 2 shows the droplet sizes from a 100 microns fused silica nozzle when sprayed using pressurized nitrogen gas as a function of distance from the nozzle tip.

The spray nozzle of the invention can be adapted to provide the desired fine mist of droplets. The nozzle can have, e.g., a conduit feeding the mixture to a capillary restrictor spray orifice that has an internal diameter of between about 50 um and about 1000 um, or about 100 um. In a preferred embodiment, the mixture comprises an emulsion of the suspension or solution in the pressurized gas or near supercritical fluid, such that when the pressure is rapidly reduced, the fluid rapidly transitions to gas, dispersing the emulsion droplets. The pressure release can be, e.g., rapid enough that the gas formation is explosive, causing the formation of fine droplets comprising the bioactive material. More specifically, it has been found that supercritical $CO_2$ assisted spraying results in the generation of ultra fine spray droplets. The droplet size has been found to vary with distance from the nozzle, as shown in FIGS. 1A and 1B. Without being bound to a particular theory, it is believed, as depicted in FIG. 1B, that the mixture sprays from nozzle 10 under low shear stress to form relatively large droplets 11 of mixture, the large droplets expand and/or effervesce in explosion area 12 to become a mist of fine suspension or solution droplets 13. For example, as shown in FIG. 1A, at distances from about 0 to about 2 cm, droplets can have an average size of about 400 µm that can be disrupted in the explosion area to a droplet size of about 10 µm only 3 cm from the nozzle orifice. Such ultrafine droplet production can also be generated, e.g., by high-pressure conventional gases at pressures of about 1000 psi or greater (see, FIG. 2).

Figure 3:
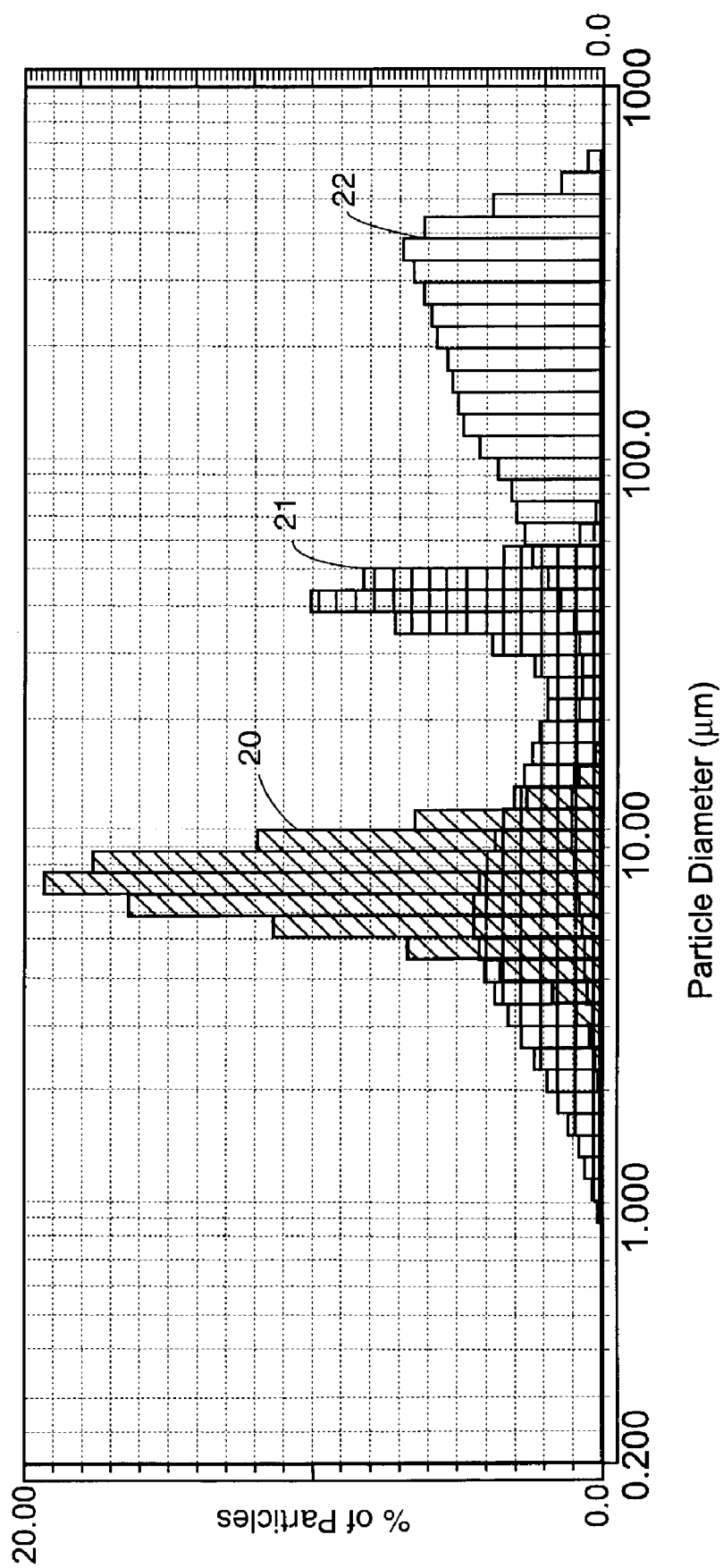
FIG. 3 shows histograms representing effects of spray pressure on particle size.

As will be appreciated by one of skill in the art, control of parameters such as particle size, size distribution, shape and form in the particulate product will be dependent upon the operating conditions used when carrying out the methods of the invention. Variables include the flow rate of the supercritical fluid, flow rate of the solution or suspension, the concentrations of the bioactive material and excipients, diameter and length of the nozzle, the surface charge on the particles, and the relative humidity, temperature, and pressure inside the particle formation chamber and secondary drying chamber. For example, as shown in FIG. 3, the size of particles can be reduced with increased spraying pressure. The histograms show that with high spraying pressure 30, the resultant particles averaged less than about 10 um, with a relatively narrow population size range. With medium spray pressure 31 the average particle size was about 45 um, and with low spray pressure 32 the particle size was about 200 um, both with relatively broad particle population size ranges.

The flow rates of the high-pressure gas/near supercritical fluid and/or the suspension/solution through the nozzle can be controlled to achieve a desired particle size, size distribution, shape, and/or form. The flow rates can be established by adjusting independent valves in the conduits, which are preferably needle valves. Flow rates can also be controlled by altering pumping conditions for the high-pressure gas/ near supercritical fluid and/or the suspension/solution. Droplets in the invention are typically produced with an average size ranging from about 1 um to about 50 um, or about 5 um, before drying into particles.

Figure 4:
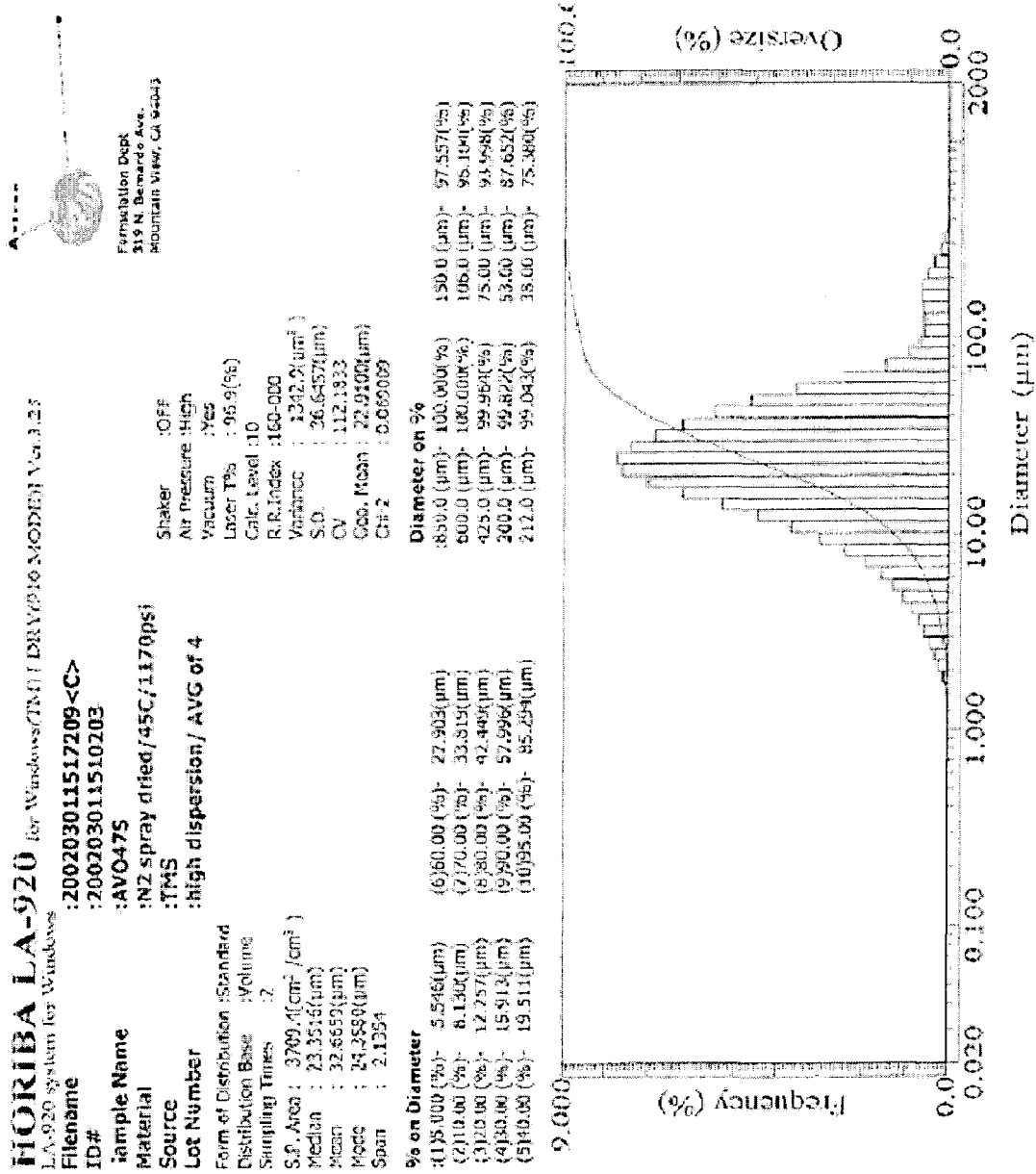
FIG. 4 shows the dry powder particle size distribution of a spray dried formulation containing B/Harbin live virus vaccine.

Near supercritical fluid is typically introduced into the mixing chamber at a near the critical pressure of the fluid. High-pressure gas is typically introduced into the mixing chamber at a pressures above about 1000 psi. The suspension or solution is typically introduced into the mixing chamber at a flow rate from about 0.5 ml/min to about 50 ml/min, or about 3 ml/min (for a 100 um capillary restrictor) to about 30 ml/min, and at a pressure near the pressure of the supercritical fluid. The mass flow ratio (gas/liquid) of the high-pressure gas or near supercritical fluid flow rate to the suspension or solution flow rate can be between about 0.1 and 100, preferably between 1 and 20, more preferably between 1 and 10, and most preferably around 5. Higher proportions and higher flow rates of suspension or solution can increase the size of the droplets and the dry particles. Dry powder particles in the invention can be controlled to have an average diameter, e.g., less than about 200 um, from about 0.5 um to about 150 um, typically from about 1 um to about 15 um; preferably, from about 3 um to about 10 um; and most preferably, from about 5 um to about 10 um, (see, FIG. 4). Droplet sizes (measured as the mass median diameter—MMD) can be controlled to have a range from about 1 um to 400 um, from about 1 um to about 200 um; preferably from about 5 um to about 50 um; and most preferably from about 3 um to about 10 um.

Pressurized gases that are suitable for spraying solutions or suspensions of the invention include, e.g. nitrogen, carbon dioxide, oxygen, propane, nitrous oxide, helium, hydrogen, and/or the like; at pressures ranging from about 100 pounds per square inch (psi) to about 15,000 psi. A number of fluids suitable for use as supercritical fluids are known to the art, including, e.g., carbon dioxide, sulfur hexafluoride, chlorofluorocarbons, fluorocarbons, nitrous oxide, xenon, propane, n-pentane, ethanol, nitrogen, water, other fluids known to the art, and mixtures thereof. The supercritical fluid is preferably carbon dioxide or mixtures of carbon dioxide with another gas such as fluoroform, and/or modifiers, such as ethanol. The temperature of pressurized gases and/or supercritical fluids mixed with suspensions or solutions in the methods can be, e.g., from about 0° C. to about 60° C. In a typical embodiment, the near supercritical fluid is $CO_2$ at a pressure of about 1000 psi. Fine particles can also be dispersed under lower carbon dioxide pressures, e.g., 500, 750 and 950, (under near-critical conditions). Near-critical fluids are defined (King, M. B., and Bott, T. R., eds. (1993), "Extraction of Natural Products using Near-Critical solvents," (Blackie Acad & Prof., Glasgow) pp. 1-33) as substances maintained at pressures between 0.9 and 1.0 of their critical pressure and/or temperature (in degree Kelvin).

The supercritical fluid can optionally contain one or more modifiers, for example, but not limited to, methanol, ethanol, isopropanol, and/or acetone. When used, the modifier preferably constitutes not more than 20%, and more preferably constitutes between 1 and 10%, of the volume of the supercritical fluid. The term "modifier" is well known to those persons skilled in the art. A modifier (or co-solvent) may be described as a chemical which, when added to a supercritical fluid, changes the intrinsic or colligative properties of the supercritical fluid in or around its critical point.

Primary drying of the droplets can begin, e.g., during the expansion of the gas-liquid mixture. Primary drying can, e.g., convert liquid droplets into primarily dried particles. Some of the solvent of the suspension or solution can be dissolved in the near supercritical fluid, e.g., even before the expansion begins. As the spray expands, the fluid can change state to a gas, removing latent heat and cooling the mist. The explosive expansion can break mixed droplets into smaller droplets. Degassing of high-pressure gases or supercritical fluids out of the droplets can further disrupt them into finer droplets. The gasses and vapors around the fine droplets can be displaced by (i.e., be exchanged with) a stream of drying gas flowing through the particle formation vessel. Significant amounts of solvent can be evaporated from the fine droplets on contact with the drying gasses; this can be accelerated by the high surface to volume ratio of the droplets, a warm temperature of the drying gas, and a low relative humidity of the drying gas. Secondary drying can take place in the particle formation vessel and/or the drying gas can carry the fine droplets and/or primarily dried particles to a secondary drying chamber for further reduction of residual moisture.

Optionally, the fine mist of droplets can be sprayed into a stream of cold fluid to freeze the droplets. The cold stream can be, e.g., a gas (e.g., $CO_2$), or a liquid (liquid nitrogen), at temperature between about −60° C. to about −200° C. The frozen droplets can be exposed to an environment of low pressure (i.e., a pressure less than atmospheric) to remove ice by sublimation to form, e.g., low density, lyophilized dry powder particles.

Secondary Drying

Secondary drying of the structurally stabilized and primarily dried particles can, e.g., further remove entrapped solvent, residual moisture, and/or water of molecular hydration, to provide a composition of powder particles with significantly lower moisture content that is stable in storage, e.g., for extended periods at ambient temperatures. Secondary drying can involve, e.g., suspension of particles in a vortex of drying gas, suspension of particles in a fluidized bed of drying gas, and/or application of warm temperatures to the particles in a strong vacuum for several hours to days. The rapid drying and fine particle sizes formed during spraying and primary drying can allow reduced temperatures and times for secondary drying in methods of the invention.

Figure 5:
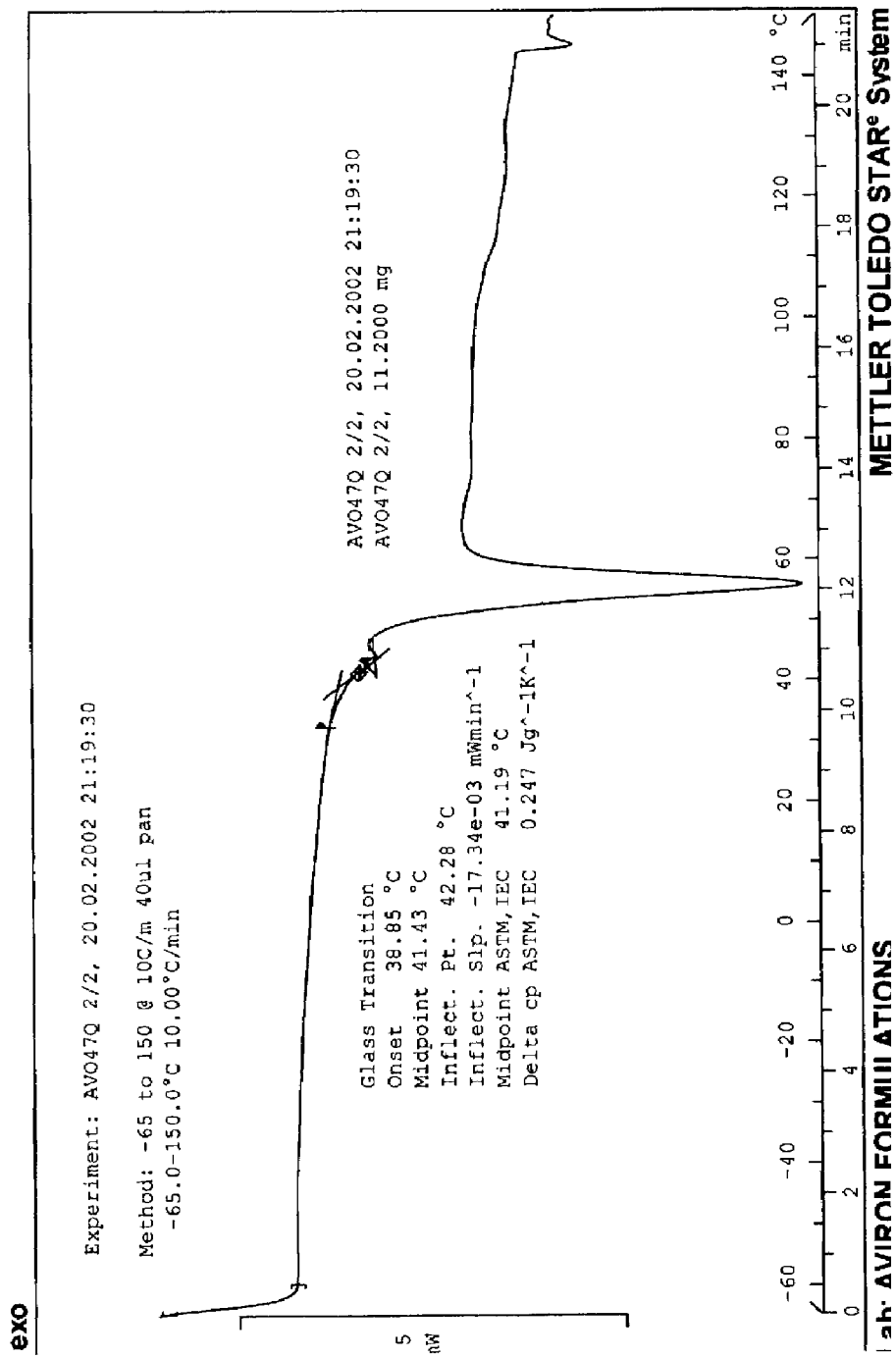
FIG. 5 shows the glass transition temperature of AVO47 formulation using differential scanning calorimeter (DSC).

Secondary drying conditions can be used, e.g., to further lower the moisture content of particles. Particles can be collected in a secondary drying chamber and held at a temperature below the glass transition temperature (See FIG. 5) of the dried (<1% moisture) formulation, or between about 5° C. and about 90° C., or between about 25° C. and about 65° C., or about 35° C. The chamber can maintain a reduced pressure and secondary drying can continue, e.g., for about 2 hours to about 5 days, or about 4 hours to about 48 hours, until residual moisture is reduced to a desired level. Secondary drying can be accelerated by providing an updraft of drying gasses in the chamber to create a fluidized bed suspension of the powder particles. Particles with lower residual moisture generally show better stability in storage with time. Secondary drying can continue until the residual moisture of the powder particles is between about 0.5 percent and about 10 percent, or less than about 5 percent. At very low residual moisture values, some bioactive molecules can be denatured by loss of water molecules of hydration. This denaturation can often be mitigated by providing alternative hydrogen binding molecules, such as sugars, polyols, and/or polymers, in the process suspension or solution.

Because of the increased efficiency of the apparatus and method described herein, drying can be achieved at relatively low temperatures compared to commonly used methods. Moreover, it has been found that during the adiabatic expansion, the temperature of the mixture decreases, i.e., the net temperature around the resulting droplets is lower because of self cooling. The temperature of the gas in the particle formation vessel and the particle collector can be maintained at or below the $T_g$ of the dried powder particle or the denaturation temperature of the biologically active material, and typically is about or less than about 90° C.; preferably, between about 25 and about 80° C.; and more preferably, between about 30 and about 50° C., or about 35° C. The reduced drying temperature can minimize activity loss from the drying process and contribute to the enhanced biological activity which is preserved in the dried fine particles recovered from the process.

The drying gas can be recycled and conditioned to provide desired drying conditions. The drying gas can be a substantially inert gas, such as nitrogen, to avoid chemical degradation of the bioactive material during drying. The gas can be cycled from the particle formation vessel and/or secondary drying chamber, through desiccators or condensers to remove humidity, through heat exchangers to heat or cool the gas to provide the desired drying temperature, and recycled, e.g., back to the particle formation chamber. An ion generator can inject ions into the stream of particles to reduce charge build up and/or to control the agglomeration rate of fine particles into larger particle sizes.

Figure 6:
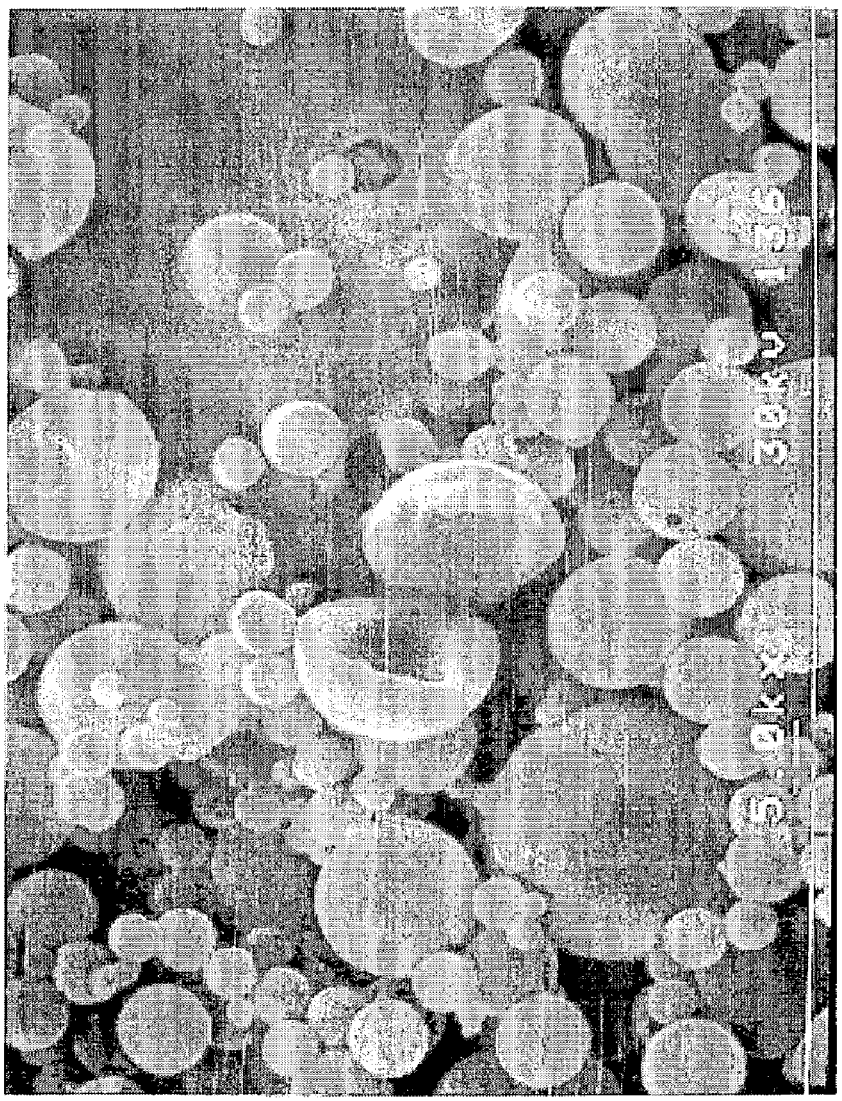
FIG. 6 shows the morphology of an exemplary spray dried powder.

Powder particles of the invention can have a size on drying, e.g., suitable to the handling, reconstitution, and/or administration requirements of the product. For example, powder particles of bioactive materials for administration by intranasal delivery by inhalation can be larger, at between about 20 um to about 150 um, than for deep pulmonary delivery by inhalation, at between about 0.1 um to about 10 um. The particle size for products that reconstitute slowly can be smaller to speed dissolution of the particles. Spray freeze-dried particles can have, e.g., a lower density, because ice can be removed from droplets without collapse of a cake structure supported by the remaining solids. Such particles can have, e.g., a physically larger size for inhaled administration due to their lower aerodynamic radius. Under some process conditions, the powder particles in the invention can have a hollowed hemispherical shape (see FIG. 6). Freeze-dried particles can, e.g., be larger than particles dried from liquid droplets and still retain quick reconstitution properties due to the porous nature of freeze-dried particles. Powder particles of the invention can have average physical diameters, e.g., between about 0.1 um and about 200 um, between about 1 um and about 50 um, or between about 2 um and about 20 um (See FIG. 4).

During the secondary drying process, e.g., a spray coat or other protective coating can be applied to the particles. For example, a mist of a polymer solution can be sprayed into a suspension of drying particles in a vortex or fluidized bed.

The methods of the invention result in a pharmaceutically-acceptable, powder particles comprising, e.g., at least one biologically active material within the amorphous glassy matrix. Preferably, the composition is almost completely dry. Some water or other aqueous solvent can remain in the composition but typically, not more than about 5% residual moisture remains by weight. The drying temperature can range from less than about 90° C., between about 25° C. and about 80° C., between about 30° C. and about 50° C. or about 35° C. A typical secondary drying process can include, e.g., raising the temperature to a drying temperature of from about 30° C. to about 55° C., and holding for from about 0.5 days to about 5 days to provide a stable dried powder composition with 0.1% to about 5%, or about 3% residual moisture. As used herein, "dry", "dried", and "substantially dried" encompass those compositions with from about 0% to about 5% water. Preferably, the powder matrix will have a moisture content from about 0.1% to about 3% as measured using the Karl Fisher method.

Figure 7:
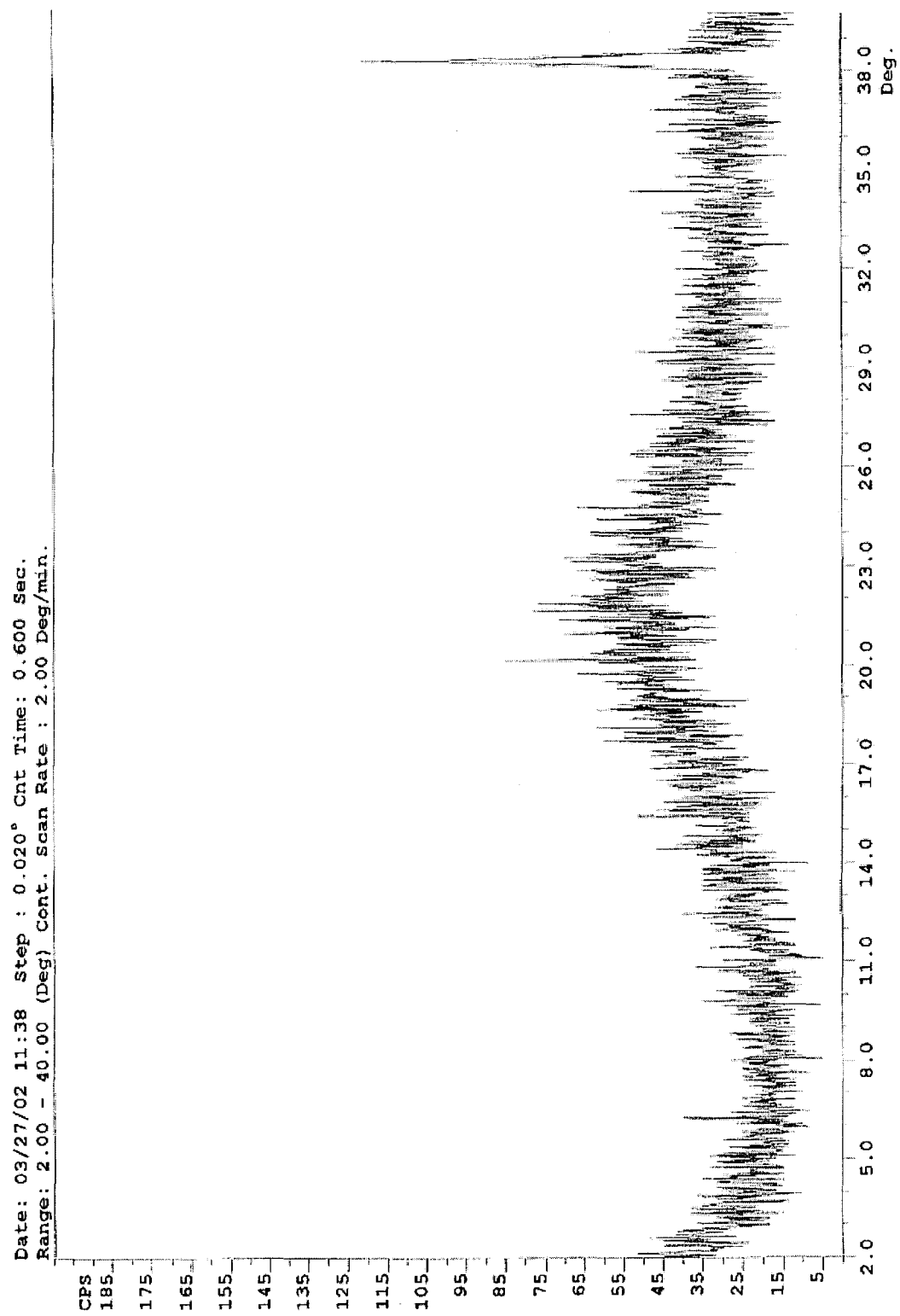
FIG. 7 shows the x-ray diffraction data of spray dried powder formulation AVO47. The diffraction pattern showed glassy amorphous nature of the AVO47 formulation

The resulting product can be an amorphous solid (see, X-ray crystallography chart, FIG. 7), wherein the glassy excipient material, e.g. sucrose, is in an amorphous glassy state and encases the biologically active material, thereby substantially restricting molecular mobility and preventing protein unfolding. Without being bound to any particular theory, this process has been postulated to occur either via mechanical immobilization of the protein or the active ingredient by the amorphous glass or via hydrogen bonding to polar and charged groups on the protein, i.e. via water replacement, thereby preventing drying induced denaturation and inhibiting further unwanted or degradative interactions. The glassy matrix stabilization theory has provided a useful albeit simplified way of describing the general phenomenon of biopreservation. However, data accumulated from the literature in the recent years have suggested that in a number of instances, the glassy state is neither necessary nor sufficient for long term stabilization. It is important to note that the mechanisms attributed to stabilization of biologicals can be multifactorial and not limited to the amorphous nature of the powder matrix in which the active ingredient is encased. Stabilization under the process described here can involve a number of factors including but not limited to the thermal history that the biomaterial is subjected to, the reduction in conformational mobility and flexibility of the protein side chains and/or reduction in the free volume as a result of the encasement, improvement in the structural rigidity of the matrix, reduction in the phase separation of excipient from the active ingredient, improvement in the degree of water displacement by selecting the optimal hydrogen bonding donor. The latter is a function of the affinity and avidity of the excipient for the surface of the protein, nucleic acids, carbohydrate, or lipids being stabilized. In general, as long as the solid is at a temperature below its glass transition temperature and the residual moisture remaining in the excipients is relatively low, the labile proteins and/or bioactive material containing lipid membranes can remain relatively stable.

Recovery of Bioactive Material in Particles

Powder particles of the invention are recovered with desired activity and in a form suitable to the intended route of administration. Powder particles of the invention can be physically recovered from the process stream, e.g., by settling or filtration after drying. The methods of the invention can provide high recovery of active and stable material due to the moderate process conditions involved. Methods of the invention can provide, e.g., particles adapted for administration as a high concentration solution, an aerosol mist, intranasal deposited particles, or pulmonary deposited particles.

Physical recovery of powder particles can depend, e.g., on the amount of material retained or expelled by the spray-drying equipment, and losses incurred due to particle size selection methods. For example, process material containing the bioactive material can be lost in the plumbing, and on surfaces of the spray-drying equipment. Solutions or particles can be lost in the process, e.g., when an agglomeration of spray droplets grows and falls out of the process stream, or when under sized droplets dry to minute particles that are carried by drying gasses through the secondary drying chamber in a process waste stream. Process yields (the percent recovery of input active material through the process) of the invention can range, e.g., from more than about 70 percent, or about 80 percent to about 98 percent, or about 90 percent.

Particles of a desired average size and size range, can be selected, e.g., by filtration, settling, impact adsorption, and/or other means known in the art. Particles can be sized by screening them through one or more filters with uniform pore sizes. Large particles can by separated by allowing them to fall from a suspension of particles in a moving stream of liquid or gas. Large particles can also stick by inertial impact to surfaces at the outside of a turning fluid stream while the stream carries away smaller or less dense particles. Smaller particles can be separated by allowing them to be swept away in a stream of liquid or gas moving at a rate at which larger particles settle.

Recovery of active bioactive material can be affected, e.g., by physical losses, cell disruption, denaturation, aggregation, fragmentation, oxidation, and/or the like, experienced during the spray-dry process. The recovery of bioactive material activity in the process is the product of the physical recovery times the specific activity of recovered material. The difference between the input activity and the recovered activity is sometimes referred to as "process loss". The methods of the invention offer reduced process loss, e.g., by converting more of the bioactive material into power particles that meet process specifications. The methods of the invention also offer improved specific activity (active bioactive material/inactive bioactive material) in powder particle final product over the prior art, e.g., by providing spray dry techniques that reduce shear stress, reduce drying time, reduce drying temperatures, and/or enhance stability. The specific activity (e.g., ratio of an active protein or viable virus over the total protein or total virus particles) can remain relatively constant through the particle formation processes of the invention. The change in specific activity of bioactive agents through the process can be, e.g., less than about 2%, less than about 10%, less than about 30%, or less than about 50%.

Administration of Bioactive Materials

Where it is appropriate, the bioactive material of the invention can be administered, e.g., to a mammal. Bioactive materials of the invention can include, e.g., peptides, polypeptides, proteins, viruses, bacteria, antibodies, cells, liposomes, and/or the like. Such materials can act as therapeutics, nutrients, vaccines, pharmaceuticals, prophylactics, and/or the like, that can provide benefits on administration to a patient, e.g., by gastrointestinal absorption, topical application, inhalation, and/or injection.

The bioactive material can be administered to a patient by topical application. For example, the powder particles can be mixed directly into a salve, carrier ointment, pressurized liquid, gaseous propellants, and/or penetrant, for application to the skin of a patient. Alternately, the powder particles can, e.g., be reconstituted in an aqueous solvent before admixture with other ingredients before application.

Bioactive materials of the invention can be administered by inhalation. Dry powder particles less than about 10 um in aerodynamic diameter can be inhaled into the lungs for pulmonary administration. Optionally, powder particles of about 20 um, or greater, in aerodynamic diameter can be administered intranasally, or to the upper respiratory tract, where they are removed from the air stream by inertial impact onto the mucus membranes of the patient. The powder particles can alternately be reconstituted to a suspension or solution for inhalation administration as an aqueous mist.

Bioactive materials of the invention can be administered by injection. The powder particles can be administered directly under the skin of a patient using, e.g., a jet of high pressure air. More commonly, the powder particles can be, e.g., reconstituted with a sterile aqueous buffer for injection through a hollow syringe needle. Such injections can be, e.g., intramuscular, intra venous, subcutaneous, intrathecal, intraperitoneal, and the like, as appropriate. Powder particles of the invention can be reconstituted to a solution or suspension with a bioactive material concentration, e.g., from less than about 0.1 ng/ml to from less than about 1 mg/ml to about 500 mg/ml, or from about 5 mg/ml to about 400 mg/ml, as appropriate to the dosage and handling considerations. Reconstituted powder particles can be further diluted, e.g., for multiple vaccinations, administration through IV infusion, and the like.

The appropriate dosage ("therapeutically effective amount") of the biologically active material will depend, for example, on the condition to be treated, the severity and course of the condition, whether the biologically active material is administered for preventive or therapeutic purposes, previous therapy, the patient's clinical history and response to the biologically active material, the type of biologically active material used, and the discretion of the attending physician. The biologically active material is suitably administered to the patent at one time, or over a series of treatments, and may be administered to the patent at any time from diagnosis onwards. The biologically active material may be administered as the sole treatment or in conjunction with other drugs or therapies useful in treating the condition in question.

As a general proposition, the therapeutically effective amount of the biologically active material administered will be in the range of about 0.00001 (e.g., in the case of a live attenuated virus vaccine) to about 50 mg/kg of patent body weight whether by one or more administrations, with the typical range of protein used being from less than about 0.01 ng/kg to about 20 mg/kg, more preferably about 0.1 mg/kg to about 15 mg/kg, administered daily, for example. However, other dosage regimens may be useful. The progress of this therapy is easily monitored by conventional techniques.

The invention also encompasses methods of increasing the "shelf-life" or storage stability of dried biologically active materials stored at elevated temperatures. Increased storage stability can be determined by recovery of biological activity in accelerated aging trials. The dry particle compositions produced by methods of the invention can be stored at any suitable temperature. Preferably, the compositions are stored at about 0° C. to about 80° C. More preferably, the compositions are stored at about 20° C. to about 60° C. Most preferably, the compositions are stored at ambient temperatures.

Compositions of the Invention

Compositions of the invention include, e.g., formulations for the suspensions and solutions used in the process methods of the invention, and the stable powder particle products of bioactive materials preserved in a matrix with polyols and/or other excipients. The compositions can be, e.g., suspensions or solutions suitable for spraying (liquid feed material) with high-pressure gas or with a near supercritical fluid to provide dry particles with improved stability. The suspensions or solutions of bioactive material can comprise, e.g., a polyol, a polymer, and/or a surfactant.

Suspensions or Solutions for Spraying of Dry Powder Particles

Formulations for preparation of dry powder particle compositions of the invention can include, e.g., bioactive materials, polymers, amino acids, polyols, surfactants, and/or buffers. Such formulations can be processed according to methods of the invention to provide stable compositions for storage and administration of the bioactive materials. For example, a composition of the invention can be an aqueous suspension of influenza virus with sucrose, HES, and block copolymers of polyethylene and polypropylene glycol (Pluronic), for spray drying with near supercritical carbon dioxide.

Bioactive materials of the invention include, e.g., materials with detectable bioactivity in living systems, biological cells and molecules used in analysis, biological cells and molecules used in medicine, biological cells and molecules used in research, and/or the like. For example, bioactive materials of the compositions of the invention include proteins, peptides, nucleic acids, bacteria, cells, antibodies, enzymes, serums, vaccines, liposomes, viruses, and/or the like.

Bioactive materials in the powder particles of the invention can be, e.g., highly pure and active at the time of drying the powder particles, due to the reduced shear stress, the low drying temperatures, and the short drying times used in their preparation. Bioactive materials are, e.g., stable in the powder particles due to the low initial process degradation and the protective aspects of the composition excipients. Bioactive materials of the composition can be, e.g., reconstituted at high concentrations without degradation due to the high surface to volume ratio of the particles and the solubility enhancements provided by the excipients of the composition.

Solutions or suspensions spray-dried to form the powder particles of the invention contain, e.g., the bioactive materials of the invention in an amount ranging from less than about 0.1 ng/ml to about 200 mg/ml, from less than about 0.5 mg/ml to about 150 mg/ml, from about 10 mg/ml to about 80 mg/ml, or about 50 mg/ml. Bioactive materials in the dry powder particles of the invention are generally present in amounts ranging, e.g., from less than about 0.01 weight percent to about 80 weight percent, from about 40 weight percent to about 60 weight percent, or about 50 weight percent. Bioactive materials of the reconstituted composition can be present in concentrations generally ranging, e.g., from less than about 0.1 ng/ml to about 500 mg/ml, from about 0.5 mg/ml to about 400 mg/ml, or about 1 mg/ml.

Bioactive materials can include complex materials with lipid membranes, such as, e.g., biologically active, viable or non-living, cells, viruses, and/or liposomes. For example the bioactive materials can include vaccines, viruses, liposomes, bacteria, platelets, and cells. Viral bioactive agents can include, e.g., influenza virus, parainfluenza virus, human metapneumovirus, respiratory syncytial virus, herpes simplex virus, SARS virus, corona virus family members, cytomegalovirus, and/or Epstein-Barr virus which can be present in the suspensions or solutions of the invention in amounts ranging from about $10^3$ TCID$_{50}$/mL to about $10^{12}$ TCID$_{50}$/mL, or about $10^6$ TCID$_{50}$/mL. Viral bioactive materials will generally be present in the suspensions or solutions in an amount of less than about 1%; more preferably, less than about 0.001%; and most preferably, less than about 0.0001% by weight. Dried powder particle compositions of the invention can provide virus present in an amount, e.g., from about $10^1$ TCID$_{50}$/g to not more than about $10^{12}$ TCID$_{50}$/g. Dried powder particle compositions can provide virus present in an amount, e.g., of about $10^1$ TCID$_{50}$/g, about $10^2$ TCID$_{50}$/g, about $10^3$ TCID$_{50}$/g, about $10^4$ TCID$_{50}$/g, about $10^5$ TCID$_{50}$/g, about $10^6$ TCID$_{50}$/g, about $10^7$ TCID$_{50}$/g, about $10^8$ TCID$_{50}$/g, about $10^9$ TCID$_{50}$/g, about $10^{10}$ TCID$_{50}$/g, or about $10^{11}$ TCID$_{50}$/g.

Polyols of the invention can include, e.g., various sugars, carbohydrates, and alcohols. For example, the polyols can include non-reducing sugars, sucrose, trehalose, sorbose, melezitose, and/or raffinose. The polyols can include, e.g., mannose, maltose, lactose, arabinose, xylose, ribose, rhamnose, galactose and glucose, mannitol, xylitol, erythritol, threitol, sorbitol, glycerol, L-gluconate, and/or the like. Where it is desired that the formulation be freeze-thaw stable, the polyol is preferably one which does not crystallize at freezing temperatures (e.g. −20° C.) such that it destabilizes the biologically active material in the formulation. The amount of polyol used in the suspension or solution can vary depending on the nature of the bioactive material, the type of polyol, and the intended use. However, generally, the final concentration of polyol is between about 1% and 40%; more preferably, between about 1% and 20% by weight. In a particularly preferred embodiment, the suspension or solution comprises about 10% sucrose.

Polymers of the invention can include, e.g., various carbohydrates, polypeptides, linear and branched chain hydrophilic molecules. For example, polymers of the formulation can include oxidized starch, carboxymethyl starch and hydroxyethyl starch (HES), dextran, non-recombinant human serum albumin (HSA), as well as nonhydrolyzed and hydrolyzed gelatin, gelatin, ovalbumin, collagen, chondroitin sulfate, a sialated polysaccharide, actin, myosin, microtubules, dynein, kinetin, alginate, and/or the like. These additives do not necessarily solely stabilize the biologically active material against inactivation; they also may help to prevent the physical collapse of the spray dried material during primary drying, lyophilization, secondary drying, and/or subsequent storage in the solid state. Preferably, HES is used with a molecular weight of between about 100,000 and 300,000; and more preferably, about 200,000. Generally, the concentration of HES can be from about 0.5% to about 10%; more preferably, between about 1 and 5% of the suspension or solution by weight. A preferred formulation comprises about 5% HES.

Suspensions or solutions for preparation of the compositions of the invention can include, e.g., one or more surfactants to aid in solubility and stability of formulation constituents. Surfactants can be present in formulations of the invention in a concentration ranging from about 0.001 weight percent to about 5 weight percent, or about 0.01 weight percent to about 1 weight percent. The surfactants can include, e.g., nonionic detergents, such as polyethylene glycol sorbitan monolaurate (Tween 20), polyoxyethylenesorbitan monooleate (Tween 80), block copolymers of polyethylene and polypropylene glycol (Pluronic), and/or the like.

Examples of suitable non-ionic surfactants are alkylphenyl alkoxylates, alcohol alkoxylates, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, fatty acid amides, methylcellulose, fatty acid esters, silicone oils, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers and mixtures of these, polyacrylates and acrylic acid graft copolymers. Other nonionic surfactants are known per se to those skilled in the art and have been described in the literature. Preferred substances are polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers and mixtures of these. Particularly preferred surfactants include polymers of a mixture of polyoxyethylene and polyoxypropylene such as Pluronic F68 (available from BASF).

Examples of suitable ionic surfactants are alkylarylsulfonates, phenylsulfonates, alkyl sulfates, alkyl sulfonates, alkyl ether sulfates, alkyl aryl ether sulfates, alkyl polyglycol ether phosphates, polyaryl phenyl ether phosphates, alkylsulfosuccinates, olefin sulfonates, paraffin sulfonates, petroleumsulfonates, taurides, sarcosides, fatty acids, alkylnaphthalenesulfonic acids, naphthalenesulfonic acids, lignosulfonic acids, condensates of sulfonated naphthalenes with formaldehyde or with formaldehyde and phenol and, if appropriate, urea, lignin-sulfite waste liquor, including their alkali metal, alkaline earth metal, ammonium and amine salts, alkyl phosphates, quaternary ammonium compounds, amine oxides, betaines and mixtures of these. Preferred substances include Pluronic F68 or Pluronic F188 with polyoxyethylene sorbitan monolaurate (i.e., Tween 20, available from Sigma) being particularly preferred.

Amino acid excipients can be present, e.g., to enhance stability, control the pH, affect reconstitution rate, serve as bulking agents, scavenge oxidizing molecules, etc. Examples of suitable amino acids are arginine, lysine, methionine, histidine, glycine, glutamic acid, and/or the like.

Buffers can be present, e.g., to control pH, enhance stability, affect constituent solubility, provide comfort on administration, and the like, in formulations for preparation of dry powder compositions. Formulation pH can be controlled in the range of about pH 3 to about pH 10, from about pH 6 to about pH 8, or about pH 7.2. Preferred buffers are often paired acid and salt forms of a buffer anion generally recognized as safe for the particular route of administration of the bioactive material. Typical buffers for use in the formulations and compositions of the invention include, e.g., amino acids, potassium phosphate, sodium phosphate, sodium acetate, sodium citrate, sodium, succinate, ammonium bicarbonate, carbonates, and the like. Generally, buffers are used at molarities from about 1 mM to about 2 M, with from about 2 mM to about 1 M being preferred, and from about 10 mM to about 0.5 M being especially preferred, and 25 to 50 mM being particularly preferred.

Exemplary formulations for suspensions with influenza virus include the following. Influenza virus in aqueous suspension with 10% sucrose, 5% hydroxyethyl starch (Fesnius), 2 mM methionine, 50 mM KH2PO4 buffer (pH 7.2), and 0.1% Pluronic F-68. Influenza virus in aqueous suspension with 10% sucrose, 5% hydroxyethyl starch, 75 mM KH2PO4 buffer (pH 7.2), 2 mM methionine, and 0.01% Pluronic F-68. Influenza virus in aqueous suspension with 5% sucrose, 2% trehalose, 0.2% Pluronic-F68; 10 mM methionine, 2% arginine, 2 mM EDTA, and 50 mM KH2PO4 buffer (pH 7.2).

In one embodiment, the formulation contains the above-identified agents (i.e., biologically active material, polyol, surfactant, and gelatin) and is essentially free of one or more preservatives, such as benzyl alcohol, phenoly, m-cresol, chlorobutanol, and benethonium chloride). In another embodiment, a preservative may be included in the formulation, particularly when the formulation is a multidose formulation.

One or more pharmaceutically acceptable carriers, excipients, or stabilizers such as those described in Remington's Pharmaceutical Sciences $16^{th}$ Edition, Osol, A. Ed. (1980) may be included in the formulation provided that they do not adversely affect the desired characteristics of the formulation. Acceptable carriers, excipients or stabilizers are non-toxic to recipients at the dosages and concentrations employed and include; additional buffering agents; co-solvents; salt-forming counterions such as potassium and sodium; antioxidants, such as methionine, N-acteyl cysteine, or ascorbic acid; chelating agents, such as EDTA or EGTA. Amino acids, such as, e.g., arginine and methionine can be included in the formulations. Arginine can be present in the formulations in an amount ranging from about 0.1 weight percent to about 5 weight percent. Methionine can be present in the formulation in a concentration ranging from about 1 mM to about 50 mM or about 10 mM. Glycerol can be present in the formulation in a concentration ranging, e.g., from about 0.1 weight percent to about 5 weight percent, or about 1 weight percent. EDTA can be present in the formulation in a concentration ranging, e.g., from about 1 mM to about 10 mM, or about 5 mM.

The present invention includes articles of manufacture comprising a container containing dried powder particles prepared by spray drying a mixture of pressurized gas or near supercritical gas with a suspension or solution of bioactive material, a polyol, a polymer additive, and a surfactant. In an embodiment of the invention, an article of manufacture is provided comprising a container which holds the pharmaceutical formulation of the present invention and optionally provides instructions for its use. Suitable containers include, for example, bottles, vials, blister packs, and syringes. The container can be formed from a variety of materials such as glass or plastic. An exemplary container is a 3-20 cc single use glass vial. Alternatively, for a multidose formulation, the container may be 3-100 cc glass vial. The container holds the formulation and the label on, or associated with, the container may indicate directions for use. The article of manufacture may further include other materials desirable from a commercial and user standpoint, including other buffers, diluents, filters, needles, syringes, and package inserts with instructions for use.

Figure 8:
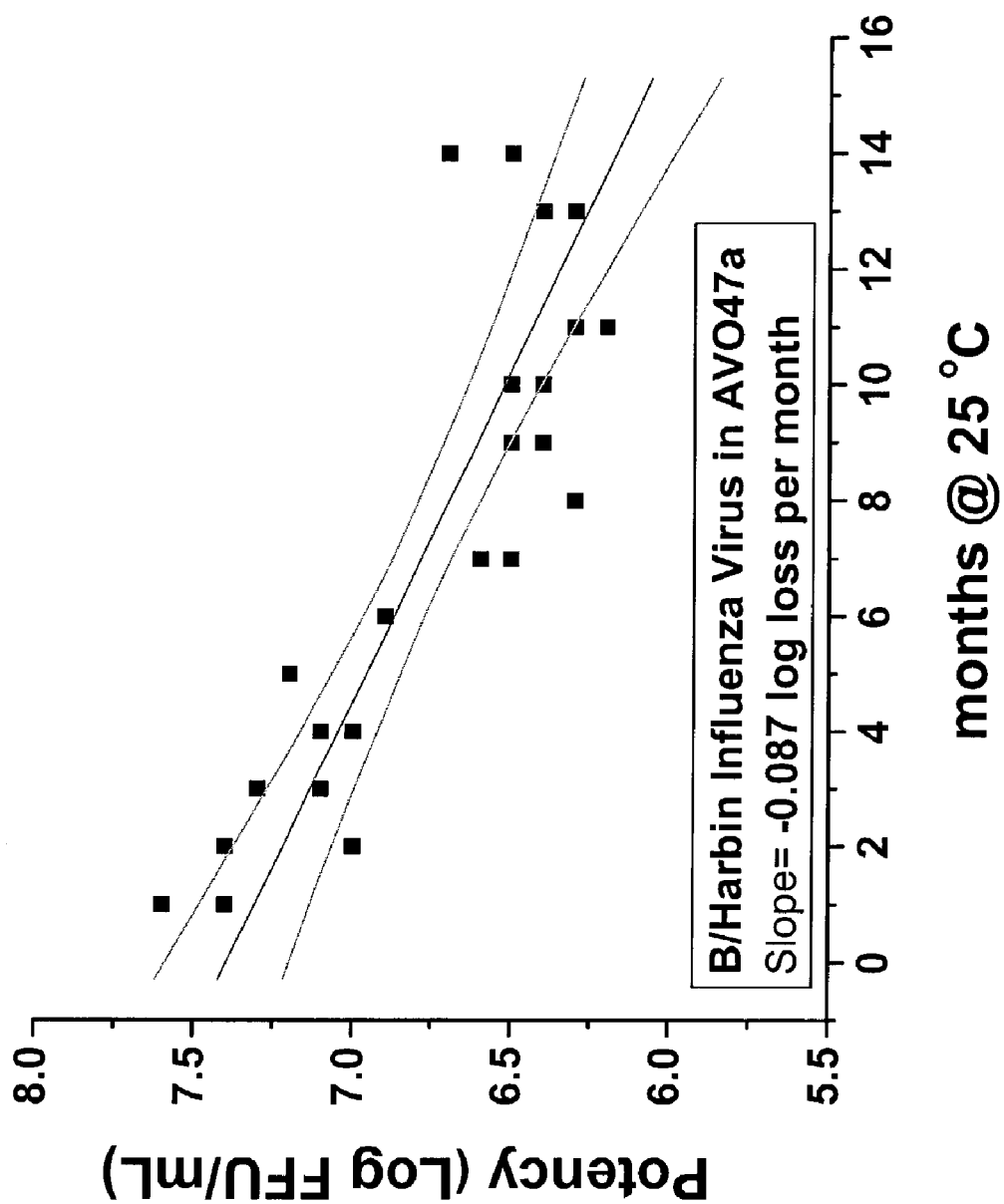

The powder particles described herein are stable, i.e., they retain their biological activity and are chemically and/or physically stable. The powder particles were tested for stability by subjecting them to aging at elevated temperature (e.g., 37° C.) and measuring their biological activity, chemical and/or physical stability. Results of these studies demonstrate that these particles which were dried at 55° C. using the methods of the invention were stable for at least nine months at 25° C. (see, FIG. 8). Particles which were dried at 35° C. were stable for at least about 13 months at 25° C. and for 2 years or more at 4° C. Such powder particles are stable even when high concentrations of the biologically active material are used. Thus, these dry particles are advantageous in that they may be shipped and stored at temperatures at or above room temperature for long periods of time.

Apparatus of the Invention

The apparatus of the invention can include, e.g., a container (first chamber) to hold the suspension or solution, a pressure vessel (second chamber) to hold a high-pressure gas and/or near supercritical fluid, conduits with control valves to control flow from the first and second chambers into a mixing chamber, a nozzle with a capillary restrictor through which a mixture can be sprayed into a particle formation vessel, and a flow of drying gas that can provide primary and/or secondary drying of particles from the particle formation vessel. Secondary drying of particles can include, e.g., settling to a warm surface in a vacuum, lyophilization of frozen particles, suspension in a vortex of drying gas, and/or suspension in a fluidized bed of drying gas.

Figure 9:
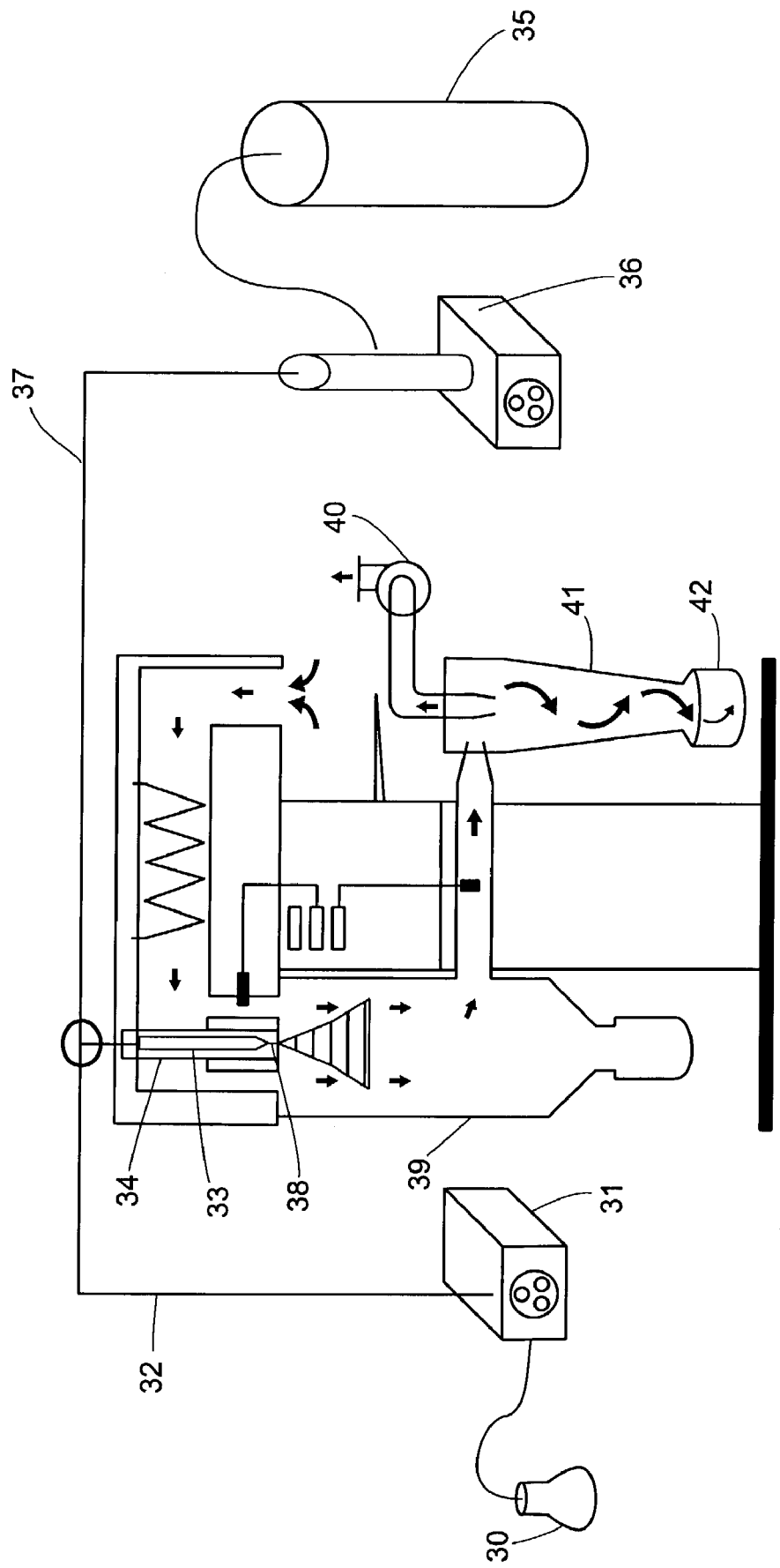
FIG. 9 is a diagrammatic drawing of an exemplary supercritical CO2 spray drying system.

As shown, for example, in FIG. 9, the apparatus can comprise, e.g., a spray nozzle directing a mist of droplets into a spray dryer. A virus suspension in first chamber 30 can be pumped by HPLC pump 31 through first conduit 32 to a T-intersection and into mixing chamber 33 of spray nozzle 34. A pressurized gas or near supercritical $CO_2$ fluid in second chamber 35 can be pumped by high pressure pump 36 capable of providing a selected pressure (e.g., from about 250-15000 psi) through second conduit 37 to the T-intersection to mix with the suspension in the mixing chamber. The mixture can be ejected from the mixing chamber through capillary restrictor 38 to form a spray mist of fine droplets that dry into particles in particle formation chamber 39. A drying gas, driven by fan 40, can displace gas and solvent vapors from the spray to provide primary drying to the particles while, e.g., carrying them to secondary drying chamber 41. Primarily dried particles from the particle formation chamber can experience secondary drying by contact with the drying gas before and after settling into particle collection vessel 42. The spray nozzle can be adapted to function with a variety of spray dryers and can be scaled to accommodate processes spraying up to several liters per hour. Spray dryer components of the apparatus can be adapted from, e.g., lab bench spray dryers made by Buchi (Brinkmann Instruments).

Certain chambers and vessels of the apparatus can have multiple or alternate functions to carry out the methods of the invention. For example, in some embodiments, the particle formation vessel can also act as a secondary drying chamber, and/or a particle collection vessel. Optionally, the secondary drying chamber can comprise a vortex chamber, fluidized bed chamber, a particle sizing chamber, a polymer coating chamber, and/or a particle collection vessel.

Fluids and Gasses

The apparatus of the invention can have chambers and conduit to hold and transfer the high-pressure gas or near supercritical fluids, and suspensions or solutions, to a mixing chamber. The sprayed droplets can experience primary and secondary drying, e.g., by contact with drying gases.

The high-pressure gases and/or near supercritical fluids can be those described in the Methods section and Compositions section above, such as nitrogen, carbon dioxide, sulfur hexafluoride, chlorofluorocarbons, fluorocarbons, nitrous oxide, xenon, propane, n-pentane, ethanol, nitrogen, water, and/or the like. Modifiers, such as certain alcohols can be dissolved in the supercritical fluids to, e.g., adjust the solvent, critical point and/or expansion properties of the fluid.

The suspensions or solutions can include a bioactive material and a polyol. Exemplary bioactive materials include proteins, peptides, nucleic acids, bacteria, cells, antibodies, enzymes, serums, vaccines, liposomes, and viruses. Polyols in the suspensions or solutions of the apparatus include, e.g., trehalose, sucrose, sorbose, melezitose, glycerol, fructose, mannose, maltose, lactose, arabinose, xylose, ribose, rhamnose, palactose, glucose, mannitol, xylitol, erythritol, threitol, sorbitol, and raffinose.

The suspensions or solutions of the apparatus can include additional excipients, such as polymers and surfactants. The polymers can be, e.g., starch, starch derivatives, carboxymethyl starch, hydroxyethyl starch (HES), dextran, human serum albumin (HSA), and/or gelatin. The surfactants can be, e.g., polyethylene glycol sorbitan monolaurate, polyoxyethylenesorbitan monooleate, block copolymers of polyethylene and/or polypropylene glycol.

Apparatus Hardware

The apparatus of the invention can include, e.g., a first chamber to hold a suspension or solution, a second chamber to hold a high-pressure gas and/or near supercritical fluid, a nozzle with a mixing chamber and a capillary restrictor with an outlet orifice, a particle formation chamber, and a secondary drying chamber. Suspension or solution can be pumped into the mixing chamber under pressure through a first conduit to mix with near supercritical fluid pumped into the mixing chamber through a second conduit. The mixture can spray out of the nozzle as a mist into the particle formation chamber where it can begin to dry on contact with a stream of drying gas. Secondary drying can take place by contact with warmed chamber walls and/or by contact with the stream of drying gas in the particle formation vessel and/or a secondary drying chamber.

In a preferred embodiment, the particle formation vessel and/or secondary drying chamber are housed within an environmental control chamber. The controlled humidity and temperature of the environmental control chamber can be the source of drying gases. Inlet gas from the environmental control chamber to the particle formation vessel can be mixed with droplets emitted from the capillary constrictor as a fine mist. The fine mist can be partially dried (i.e., from a droplet into a particle) in the particle formation vessel before transfer in a stream of drying gas to a secondary drying chamber, such as a cyclonic vortex chamber. The stream of drying gas can continue to a gas outlet port back into a environmental control chamber where the gas can be reconditioned. The apparatus can further comprise a desiccant or condenser system for removing moisture from the gas and/or the environmental control chamber. A heat exchanger can be used to control the temperature of the recycled gas and prevent excessive build up of temperature inside the environment controlled chamber. Typically, the chamber is cooled by introduction of liquid nitrogen from a liquid nitrogen reservoir with control by an optional temperature controller which can automatically meter the liquid nitrogen to provide for a relatively invariant temperature inside the environmental control chamber. Optionally, the environmental control chamber can be cooled by a refrigeration heat exchanger (evaporator). The environmental control chamber is typically vented to the ambient room pressure via a pressure control port which can be valved or pressure gated. Spray drying into a reduced moisture controlled gas can provide a large moisture differential between the sprayed droplets and the drying chamber environment. The effect can be a reduced input heat requirement for the primary drying phase.

The first and second chambers can be pressurized, and/or pumps can be employed in the conduits, to deliver high-pressure gas and/or near supercritical fluid, and/or suspensions or solutions, to the mixing chamber. The rate of delivery can be controlled by means commonly practiced in the art, such as, e.g., by controlling the pumping rate or by controlling valves in the conduits. The pumps can be any type known in the art, such as, e.g., peristaltic pumps, rotary pumps, diaphragm pumps, piston pumps, and the like. Valves can be any appropriate style known in the art, including, e.g., ball and seat, diaphragm, needle, that can restrict the flow of pressurized fluids. Typically, the second container is pressurized, refrigerated and/or insulated to hold the pressurized gas or fluid at near critical conditions.

The mixing chamber can be, e.g., an enlarged space between conduit inflow ports and the capillary restrictor output orifice. The conduits can be generally directed to flow the pressurized gas and/or near supercritical fluid and suspensions or solutions into each other, to enhance mixing. The conduits can meet at a T-intersection with flows meeting head on, or at an intersection wherein flows meet at less than 180 degrees opposition, e.g., wherein the first conduit and/or second conduit direct flow at an angle less than 90 degrees from the axis of flow in the mixing chamber. Flows can meet indirectly, e.g., with an offset, to create a swirling, vortex or turbulent flow, since this can promote more thorough mixing and create more monodispersed gas-liquid emulsion, as is appreciated by those skilled in the art. The main body of the chamber can have a long aspect ratio to enhance contact surfaces between the supercritical fluid and suspensions or solutions. The mixing chamber can have passage configurations that include baffles, beads, channels, obstructions, constrictions, and/or the like, to enhance mixing of the high-pressure gas and/or supercritical fluid with the suspensions or solutions. The mixing chamber can be a conduit with an internal diameter greater than the internal diameter of the capillary restrictor. The mixing chamber can be a part of the nozzle, or a separate component of the apparatus.

The capillary restrictor can be, e.g., a conduit that provides a restriction to fluid flow to help maintain a high pressure or near supercritical conditions in the mixing chamber. The capillary restrictor can have, e.g., an outlet orifice through which the high-pressure gas/near supercritical fluid mixture with suspension or solution can be sprayed. The size of the capillary restrictor internal diameter and outlet orifice can affect the size of droplets produced in the spray; with larger droplets (and ultimately, particles) generally formed by spraying from, e.g., larger outlets. Typically, the capillary restrictor has a length from about 2 inches to about 6 inches, and an internal diameter and/or outlet diameter, e.g., of about 50 um or less, to about 1000 um, from about 50 um to about 500 um, or about 100 um.

The mixture sprays out of the nozzle into a particle formation vessel where it, e.g., expands to gases and disrupted fluid feed droplets. A drying gas can be introduced into the particle formation vessel to displace mixture gasses (expanded gases and evaporated solvents) from the droplets. The drying gasses can contact the droplets to evaporate additional solvent from them to form particles. The drying gasses can carry droplets and/or particles to other chambers for processing by the methods of the invention. For example, primarily dry particles can be suspended in a stream of drying gas in the particle formation vessel, or be carried to a separate chamber, for secondary drying, sizing, coating, and/or collection. The drying gas can be, e.g., an inert gas, such as nitrogen, at a temperature below the glass transition temperature of the powder particles. The apparatus can include heat exchangers to control the temperature of the drying gas, e.g., less than about 90° C., between about 25° C. to about 80° C., between about 30° C. and 50° C., or about 35° C. Preferred drying gas (inlet gas) temperatures during particle formation in the methods of the invention are less than 65° C., or between about 30° C. and about 55° C., or about 35° C. The apparatus can include condensers or desiccators to lower the relative humidity, or solvent level, of the drying gas, e.g., so it can be recycled or sent to waste without harm to the environment.

The particle formation vessel or a secondary drying vessel can be adapted to provide a cyclonic vortex chamber. Particles, carried in a stream of drying gas, can, e.g., enter a long cylindrical or conical chamber at one end through an offset port. The gases can swirl many times in a spiral route from the inlet end of the chamber to an outlet end. Such a route can take considerable time with the particles receiving warmth from the gas and chamber walls while they continue to lose residual moisture.

The particle formation vessel or a secondary drying vessel can be adapted to provide a fluidized bed chamber. Particles suspended in the stream of drying gas can be transferred, e.g., to an inlet at the bottom of a cylindrical chamber where they can become suspended in an updraft of the drying gas. Optionally, particles can be collected at the bottom of a chamber before directing drying gas from below to suspend the particles in a fluidized bed. The particles can remain suspended as a fluidized bed for a considerable time while residual moisture continues to be lost. Size separation can take place in the fluidized bed chamber as small particles are lost in the waste stream out the top of the chamber and large particles settle the bottom. Polymer coatings can be applied to particles, e.g., by spraying a mist of polymer solution into the fluidized bed to dry as a coat on the particles.

The particle formation vessel, or secondary drying vessel, can be adapted to provide a collection vessel for collection of dried powder particles. For example, particles flowing in a transfer conduit suspended in gas can be directed into a chamber with considerably larger diameter than the transfer conduit. The velocity of the gas can slow in the larger chamber allowing the particles to fall to the floor of the chamber while the gas exits to waste above. The particles can accumulate in a removable container at the floor of the chamber where they can be recovered for use, packaging, or storage.

The present invention includes kit comprising, e.g., elements of the apparatus and process materials facilitating practice of the methods of the invention. The kits of the invention can be a container containing an apparatus element of the invention, such as a vessel of pressurized gas or near supercritical fluid, suspension or solution components (such as bioactive material or process solutions of a polyol, a polymer, an amino acid, a surfactant, and/or a buffer), a spray nozzle, a collection vessel, and/or the like, for use in practicing methods of preparing dried particle compositions of the invention. The kit can be substantially sterilizable, e.g., made of materials tolerant of the temperature and moisture in an autoclave, tolerant of ionizing radiation, and/or tolerant of radiation produced within a microwave oven. The kits of the invention can include instructional materials teaching the use of apparatus, apparatus elements, and/or process materials of the invention to prepare dry particles of bioactive materials.

EXAMPLES

The following examples are offered to illustrate, but not to limit the claimed invention.

Example 1

Formulations for Spraying Influenza Suspensions

Formulations such as those shown below were prepared according to the methods of this invention using B/Harbin influenza virus or placebo. pH was adjusted with either sodium hydroxide or potassium hydroxide. Useful formulations for spray drying attenuated Influenza viruses can include, e.g., about 10% to about 2% trehalose, about 40% to about 5% sucrose, about 1% sorbitol, about 5% to about 2% HES, about 2% ovalbumin, about 5% to about 2% gelatin, about 1% PVP, about 2% to about 0.01% Pluronic F68, about 0.03% Tween 20, about 10 mM to about 2 mM methionine, about 5% to about 0.5% arginine, about 23 mM EDTA, about 0.5% to about 0.05% glycerol, about 10% to about 1% glutamate, and/or about 10 mM N-acetylcysteine.

|  | Polyol | Polymer Additive | Surfactant | Other |
|---|---|---|---|---|
| AV020 | 5% trehalose | 5% HES | 0.01% Pluronic F68 | 75 mM, pH 7.2 KPO4 buffer; 2 mM methionine |
| AV021 | 5% trehalose | 5% HES | 0.03% Tween 20 | 75 mM, pH 7.2 KPO4 buffer; 2 mM methionine |
| AV022 | 5% trehalose | 5% HES | 0.05% Pluronic F68 | 75 mM, pH 7.2 KPO4 buffer; 2 mM methionine |
| AV023a | 10% sucrose | 5% HES | 0.01% Pluronic F68 | 75 mM, pH 7.2 KPO4 buffer; 10 mM N-acetylcysteine |
| AV023 | 10% sucrose | 5% HES | 0.01% Pluronic F68 | 75 mM, pH 7.2 KPO4 buffer; 2 mM methionine; 2 mM EDTA; 0.5% arginine |
| AV024 | 10% sucrose | 5% HES | 0.01% Pluronic F68 | 75 mM, pH 7.2 KPO4 buffer; 2 mM methionine; 1% PVP; 0.5% arginine |
| AV025 | 5% sucrose; 2% trehalose | — | 0.05% Pluronic F68 | 50 mM, pH 7.2 KPO4 buffer; 2 mM EDTA; 2% arginine |
| AV026 | 5% sucrose; 2% trehalose | 2% HES | 0.05% Pluronic F68 | 50 mM, pH 7.2 KPO4 buffer; 2 mM EDTA; 2% arginine |

-continued

| | Polyol | Polymer Additive | Surfactant | Other |
|---|---|---|---|---|
| AV027 | 5% sucrose; 2% trehalose | — | 0.05% Pluronic F68 | 50 mM, pH 7.2 KPO4 buffer; 10 mM methionine; 2 mM EDTA; 2% arginine |
| AV028 | 5% sucrose; 2% trehalose | 2% HES | 0.05% Pluronic F68 | 50 mM, pH 7.2 KPO4 buffer; 10 mM methionine; 2 mM EDTA; 2% arginine |
| AV029 | 5% sucrose; 2% trehalose | — | 0.05% Pluronic F68 | 50 mM, pH 6.8 KPO4 buffer; 10 mM methionine; 2 mM EDTA; 2% arginine |
| AV030 | 5% sucrose; 2% trehalose | 2% HES | 0.05% Pluronic F68 | 50 mM, pH 7.2 KPO4 buffer; 10 mM methionine; 2 mM EDTA; 2% arginine |
| AV031 | 2% trehalose | 2% HES | 0.05% Pluronic F68 | 50 mM, pH 7.2 KPO4 buffer; 2 mM EDTA; 0.2% sodium thiosulphate; 2% arginine |
| AV032 | 5% sucrose; 2% trehalose | 2% HES | 0.05% Pluronic F68 | 50 mM, pH 7.2 KPO4 buffer; 10 mM methionine; 2 mM EDTA; 2% arginine |
| AV033 | 5% sucrose; 2% trehalose | | 0.05% Pluronic F68 | 50 mM, pH 7.2 KPO4 buffer; 10 mM methionine; 2 mM EDTA; 2% arginine |
| AV034 | 5% sucrose; 2% trehalose | 2% HES | | 50 mM, pH 7.2 KPO4 buffer; 10 mM methionine; 2 mM EDTA; 2% arginine |
| AV035 | 10% sucrose: 10% trehalose | | | 100 mM, pH 7.2 KPO4 buffer; 5 mM TMAO; |
| AV036 | 10% sucrose: 10% trehalose | | | 100 mM, pH 7.2 KPO4 buffer; 5 mM TMAO; 0.5% glycerol |
| AV037 | 10% sucrose: 10% trehalose | | | 100 mM, pH 7.2 KPO4 buffer; 5 mM TMAO; 0.5% glycerol |
| AV038 | 10% sucrose: 10% trehalose | | | 100 mM, pH 7.2 KPO4 buffer; 10 mM N-acetylcysteine; 0.5% glycerol |
| AV039 | 5% sucrose; 2% trehalose | 2% ovalbumin | 0.05% Pluronic F68 | 50 mM, pH 7.2 KPO4 buffer; 10 mM methionine; 10 mM N-acetylcysteine; 2 mM EDTA; 2% arginine; |
| AV040 | 5% sucrose; 2% trehalose | 2% ovalbumin | 0.05% Pluronic F68 | 50 mM, pH 7.2 KPO4 buffer; 10 mM methionine; 2 mM EDTA; 2% arginine; |
| AV041 | 5% sucrose; 2% trehalose | 2% gelatin (K&K) | 0.05% Pluronic F68 | 50 mM, pH 7.2 KPO4 buffer; 10 mM methionine; 2 mM EDTA; 2% arginine |
| AV042 | 5% sucrose; 2% trehalose | | 0.05% Pluronic F68 | 50 mM, pH 7.2 KPO4 buffer; 10 mM methionine; 5 mM TMAO; |
| AV043 | 5% sucrose; 2% trehalose | | 2% Pluronic F68 | 50 mM, pH 7.2 KPO4 buffer; 10 mM methionine; 2 mM EDTA; 2% arginine |
| AV044 | 5% sucrose; 2% trehalose | | 0.05% Pluronic F68 | 50 mM, pH 7.2 KPO4 buffer; 2 mM EDTA; 2% arginine; 1% L-glutamate |
| AV045 | 5% sucrose; 2% trehalose | | 0.1% Pluronic F68 | 100 mM, pH 7.2 KPO4 buffer; 10 mM N-acetylcysteine; 2 mM EDTA; 2% arginine |
| AV046 | 5% sucrose; 2% trehalose | | 0.1% Pluronic F68 | 100 mM, pH 7.2 KPO4 buffer; 10 mM N-acetylcysteine; 5 mM TMAO; 2 mM EDTA; 2% arginine; 0.05% glycerol |
| AV047 | 5% sucrose; 2% trehalose | | 0.2% Pluronic F68 | 50 mM, pH 7.2 KPO4 buffer; 10 mM methionine; 2 mM EDTA; 2% arginine |
| AV048 | 5% sucrose; 2% trehalose | | 0.05% Pluronic F68 | 50 mM, pH 7.2 citrate buffer; 10 mM methionine; 2 mM EDTA; 2% arginine |
| AV049 | 5% sucrose; 2% trehalose | | 0.05% Pluronic F68 | 50 mM, pH 7.2 KPO4 buffer; 10 mM methionine; 2 mM EDTA; 2% arginine |
| AV050 | 5% sucrose; 2% trehalose | | 0.05% Pluronic F68 | 50 mM, pH 7.2 KPO4 buffer; 10 mM methionine; 2 mM EDTA; 2% arginine |

-continued

|  | Polyol | Polymer Additive | Surfactant | Other |
|---|---|---|---|---|
| AV051 | 5% sucrose; 2% trehalose |  | 0.05% Pluronic F68 | 50 mM, pH 7.2 KPO4 buffer; 10 mM methionine; 2 mM EDTA; 2% arginine |
| AV052 | 5% sucrose; 2% trehalose |  | 0.05% Pluronic F68 | 50 mM, pH 7.2 KPO4 buffer; 10 mM methionine; 2 mM EDTA; 2% arginine |
| AV053 | 5% sucrose; 2% trehalose |  |  | 50 mM, pH 7.2 KPO4 buffer; 10 mM methionine; 2 mM EDTA; 2% arginine |
| AV054 | 5% sucrose; 2% trehalose | 2% HES | 0.05% Pluronic F68 | 50 mM, pH 7.2 KPO4 buffer; 10 mM methionine; 2 mM EDTA; 2% arginine |
| AV055 | 5% sucrose; 2% trehalose |  | 0.05% Pluronic F68 | 50 mM, pH 7.2 KPO4 buffer; 10 mM methionine; 2 mM EDTA |
| AV056 | 5% sucrose; 2% trehalose |  | 0.05% Pluronic F68 | 50 mM, pH 7.2 KPO4 buffer; 10 mM methionine; 2% arginine |
| AV057 | 5% sucrose; 2% trehalose |  |  | 50 mM, pH 7.2 KPO4 buffer; 10 mM methionine; 2 mM EDTA; 2% arginine |
| AV058 | 2% trehalose |  | 0.05% Pluronic F68 | 50 mM, pH 7.2 KPO4 buffer; 10 mM methionine; 2 mM EDTA; 2% arginine |
| AV059 | 5% sucrose |  | 0.05% Pluronic F68 | 50 mM, pH 7.2 KPO4 buffer; 10 mM methionine; 2 mM EDTA; 2% arginine |
| AV060 | 5% sucrose; 2% trehalose |  | 0.05% Pluronic F68 | 50 mM, pH 7.2 KPO4 buffer; 2 mM EDTA; 2% arginine |
| AV061 | 5% sucrose; 2% trehalose |  | 0.05% Pluronic F68 | 50 mM, pH 7.2 KPO4 buffer; 10 mM methionine; 2 mM EDTA; 2% arginine |
| AV062 | 6% sucrose; 1% sorbitol |  | 0.05% Pluronic F68 | 50 mM, pH 7.2 KPO4 buffer; 10 mM methionine; 2 mM EDTA; 2% arginine |
| AV063 | 7% sucrose |  | 0.05% Pluronic F68 | 50 mM, pH 7.2 KPO4 buffer; 10 mM methionine; 2% arginine |
| AV064 | 6% sucrose; 1% sorbitol |  | 0.05% Pluronic F68 | 50 mM, pH 7.2 KPO4 buffer; 10 mM methionine; 2 mM EDTA; 2% arginine |
| AV065 | 10% sucrose; 2% trehalose | 5% HES | 0.2% Pluronic F68 | 50 mM, pH 7.2 KPO4 buffer; 10 mM methionine; 2 mM EDTA; 2% arginine |
| AV066 | 5% sucrose; 2% trehalose | 2% HES |  | 50 mM, pH 7.2 KPO4 buffer; 2% arginine |
| AV067 | 10% sucrose | 2% HES |  | 50 mM, pH 7.2 KPO4 buffer; 5% arginine |
| AV068 | 10% sucrose | 2% HES |  | 50 mM, pH 7.2 KPO4 buffer; 1 mM ZnCl2; 5% arginine |
| AV070 | 40% sucrose | 5% gelatin (K&K) | 0.02% Pluronic F68 | 25 mM, pH 7.2 KPO4 buffer; 10 mM methionine; 10% L-glutamate |
| AV071 | 40% sucrose | 5% gelatin (K&K) | 0.02% Pluronic F68 | 25 mM, pH 7.2 KPO4 buffer; 10 mM methionine |
| AV047 W/HES | 5% sucrose; 2% trehalose | 2% HES | 0.02% Pluronic F68 | 50 mM, pH 7.2 KPO4 buffer; 10 mM methionine; 2 mM EDTA; 2% arginine |
| AV069 | 10% sucrose | 2% HES |  | 50 mM, pH 7.2 citrate buffer; 1 mM ZnCl2; 5% arginine |
| AV047-P | 5% sucrose; 2% trehalose |  | 0.02% Pluronic F68 | 50 mM, pH 7.2 KPO4 buffer; 10 mM methionine; 2 mM EDTA; 2% arginine |
| AV047 citrate | 5% sucrose; 2% trehalose |  | 0.02% Pluronic F68 | 50 mM, pH 7.2 citrate buffer; 10 mM methionine; 2 mM EDTA; 2% arginine |

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, the formulations, techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of preparing powder particles containing bioactive material, the method comprising:
   preparing a suspension or solution comprising the bioactive material;
   forming a mixture of the solution or suspension with a high pressure gas comprising a pressure ranging from about 250 psi to a pressure less than 90% of a critical pressure of the gas;
   reducing a pressure on the mixture, thereby spraying a biphasic gaseous suspension of droplets; and,
   drying the droplets into powder particles by exchanging a gas from the gaseous suspension of droplets with a drying gas.

2. The method of claim 1, wherein the bioactive material is selected from the group consisting of proteins, peptides, nucleic acids, bacteria, cells, antibodies, enzymes, serums, vaccines, liposomes, and viruses.

3. The method of claim 2, wherein the viruses are selected from the list consisting of influenza virus, parainfluenza virus, respiratory syncytial virus, herpes simplex virus, SARS virus, cytomegalo virus, corona virus family members, human metapneumovirus, and Epstein-Bar virus.

4. The method of claim 1, wherein the solution or suspension further comprises a polyol selected from the group consisting of: trehalose, sucrose, sorbose, melezitose, glycerol, fructose, mannose, maltose, lactose, arabinose, xylose, ribose, rhamnose, palactose, glucose, mannitol, xylitol, erythritol, threitol, sorbitol, and raffinose.

5. The method of claim 1, wherein the suspension or solution further comprises a polymer.

6. The method of claim 5, wherein the polymer is selected from the group consisting of starch, starch derivatives, polyvinyl pyrrolidone (PVP), carboxymethyl starch, hydroxyethyl starch (HES), dextran, human serum albumin (HSA), and gelatin.

7. The method of claim 1, wherein the suspension or solution further comprises a surfactant.

8. The method of claim 7, wherein the surfactant comprises polyethylene glycol sorbitan monolaurate, polyoxyethylenesorbitan monooleate, or block copolymers of polyethylene and polypropylene glycol.

9. The method of claim 1, wherein the suspension or solution further comprises an amino acid.

10. The method of claim 9, wherein the amino acid comprises arginine, lysine, methionine, histidine, or glutamic acid.

11. The method of claim 1, wherein the high pressure gas is selected from the group consisting of: nitrogen, oxygen, helium, carbon dioxide, sulfur hexafluoride, chlorofluorocarbons, fluorocarbons, nitrous oxide, xenon, propane, n-pentane, ethanol, nitrogen, and water.

12. The method of claim 11, wherein the high pressure gas comprises a pressure of about 1200 psi.

13. The method of claim 11, wherein the high pressure gas comprises a temperature ranging from about 0° C. to about 60° C.

14. The method of claim 1, wherein forming a mixture comprises flowing the solution or suspension with the high-pressure gas through a mixing chamber.

15. The method of claim 14, wherein the mixing chamber comprises passage configurations which produce vortices or turbulence in the flowing mixture.

16. The method of claim 1, wherein reducing the pressure comprises passage of the mixture through a capillary restrictor.

17. The method of claim 16, wherein the capillary restrictor comprises an internal diameter ranging from about 50 um to about 1000 um.

18. The method of claim 17, wherein the internal diameter is about 100 um.

19. The method of claim 1, further comprising flowing the suspension or solution at a rate ranging from about 0.5 ml/min to about 30 ml/min.

20. The method of claim 1, wherein the droplets range in average size from about 5 um to about 50 um.

21. The method of claim 20, further comprising modifying an average size of the droplets by: adjusting a pressure of the high pressure gas, adjusting a pressure of the suspension or solution, adjusting a flow rate of the suspension or solution, adjusting a nozzle conduit internal diameter, adjusting a temperature of a drying gas, adjusting a pressure inside a particle formation vessel, or changing a concentration of a suspension or solution constituent.

22. The method of claim 1, wherein drying comprises suspension of the powder particles in a fluidized bed.

23. The method of claim 1, further comprising injecting counter ions into a chamber of dry or drying particles.

24. The method of claim 1, wherein the drying gas is nitrogen at a temperature ranging from about 35° C. to about 90° C.

25. The method of claim 1, further comprising recycling the drying gas.

26. The method of claim 1, wherein the powder particles range in average size from about 1 um to about 150 um.

27. The method of claim 1, wherein the powder particles have a moisture content of less than about 5 weight percent.

28. The method of claim 1, wherein the bioactive material remains stable in storage at about 25° C. for at least about nine months or at about 4° C. for at least about 1 year.

29. The method of claim 1, wherein the bioactive material comprises live viruses, live bacteria, or live cells which retain at least about half an original viability in the powder particles.

30. The method of claim 1, further comprising collecting the powder particles.

31. The method of claim 30, wherein collecting comprises transferring the powder particles to a secondary drying chamber in a flowing stream of gas.

32. The method of claim 31, wherein the secondary drying chamber comprises a cyclonic vortex chamber.

33. The method of claim 30, wherein collecting comprises separation of powder particles by size.

34. The method of claim 33, wherein the separation comprises differential settling of the powder particles.

35. The method of claim 30, wherein a total process efficiency is not less than about 70%.

36. The method of claim 1, further comprising coating the powder particles with a protective coat.

37. The method of claim 1, further comprising reconstituting the powder particles into a reconstituted suspension or solution comprising a bioactive material concentration greater than the suspension or solution.

38. The method of claim 1, further comprising administering the powder particles to a mammal by intramuscular, intraperitoneal, intracerebrospinal, subcutaneous, intra-articular, intrasynovial, intrathecal, oral, topical, inhalation intranasal, or pulmonary administration routes.

39. The method of claim 1, wherein the high pressure gas comprises a pressure of about 1000 psi.

* * * * *